US011590277B2

United States Patent
Stonecipher et al.

(10) Patent No.: US 11,590,277 B2
(45) Date of Patent: Feb. 28, 2023

(54) DRUG DELIVERY DEVICE WITH ACTIVATION PREVENTION FEATURE

(71) Applicant: AMGEN INC., Thousand Oaks, CA (US)

(72) Inventors: Brian Stonecipher, Newbury Park, CA (US); Margaux Frances Boyaval, Newbury Park, CA (US); James Chan, San Marino, CA (US); Avon Kuo, San Jose, CA (US); Allan Lee Cameron, Natick, MA (US); Maxwell Franklin Bischoff, Somerville, MA (US); Gregg Allen Flender, Bedford, MA (US)

(73) Assignee: AMGEN INC., Thousand Oaks, CA (US)

( * ) Notice: Subject to any disclaimer, the term of this patent is extended or adjusted under 35 U.S.C. 154(b) by 10 days.

(21) Appl. No.: 16/488,120

(22) PCT Filed: Mar. 6, 2018

(86) PCT No.: PCT/US2018/021126
§ 371 (c)(1),
(2) Date: Aug. 22, 2019

(87) PCT Pub. No.: WO2018/165143
PCT Pub. Date: Sep. 13, 2018

(65) Prior Publication Data
US 2019/0381238 A1    Dec. 19, 2019

Related U.S. Application Data

(60) Provisional application No. 62/467,602, filed on Mar. 6, 2017.

(51) Int. Cl.
*A61M 5/14*    (2006.01)
*A61M 5/142*   (2006.01)

(52) U.S. Cl.
CPC ...... *A61M 5/1413* (2013.01); *A61M 5/14248* (2013.01); *A61M 2005/14252* (2013.01);
(Continued)

(58) Field of Classification Search
CPC .... A61M 2205/276; A61M 2005/2073; A61M 5/14248
See application file for complete search history.

(56) References Cited

U.S. PATENT DOCUMENTS 3,927,955 A    12/1975  Spinosa et al.
5,928,194 A    7/1999   Maget
(Continued)

FOREIGN PATENT DOCUMENTS

EP    2268342 A1      1/2011
JP    2016-524513 A   8/2016
(Continued)

OTHER PUBLICATIONS

International Search Report for International Application No. PCT/US2018/021126, dated Jun. 6, 2018.
(Continued)

*Primary Examiner* — Deanna K Hall
(74) *Attorney, Agent, or Firm* — Marshall, Gerstein & Borun LLP

(57) ABSTRACT

A wearable drug delivery device includes an injector having a housing, a reservoir, a needle or cannula, a drive mechanism for urging drug product out of the reservoir, through the needle or cannula, and to a patient, and an activator mechanism disposed on a surface of the housing for activating the drive mechanism. An activation prevention mechanism is coupled to the injector housing and/or activation prevention mechanism to prevent inadvertent actuation of the activator mechanism.

10 Claims, 18 Drawing Sheets

(52) U.S. Cl.
CPC . *A61M 2205/276* (2013.01); *A61M 2205/583* (2013.01); *A61M 2207/00* (2013.01)

(56) References Cited

U.S. PATENT DOCUMENTS

| | | | |
|---|---|---|---|
| 6,500,150 | B1 | 12/2002 | Gross et al. |
| 6,595,956 | B1 | 7/2003 | Gross et al. |
| 6,824,529 | B2 | 11/2004 | Gross et al. |
| 7,731,686 | B2 | 6/2010 | Edwards et al. |
| 7,749,194 | B2 | 7/2010 | Edwards et al. |
| 7,901,382 | B2 | 3/2011 | Daily et al. |
| 8,469,917 | B2 | 6/2013 | Liniger et al. |
| 9,486,297 | B2 | 11/2016 | Clayton et al. |
| 9,821,116 | B2 * | 11/2017 | Vouillamoz .......... A61M 5/3286 |
| 11,285,260 | B2 * | 3/2022 | Cole ................. A61M 5/14248 |
| 2008/0033393 | A1 | 2/2008 | Edwards et al. |
| 2013/0046239 | A1 * | 2/2013 | Gonnelli ............ A61M 5/1454 604/150 |
| 2013/0345633 | A1 * | 12/2013 | Chong ................ A61M 5/1454 604/134 |
| 2014/0031793 | A1 * | 1/2014 | Constantineau ... A61B 17/3496 604/164.12 |
| 2014/0207104 | A1 * | 7/2014 | Vouillamoz ....... A61M 5/14248 604/506 |
| 2014/0323987 | A1 * | 10/2014 | Nelson .............. A61M 5/16877 604/248 |
| 2014/0324023 | A1 | 10/2014 | Krijger et al. |
| 2015/0080799 | A1 | 3/2015 | Schneider et al. |
| 2016/0106584 | A1 | 4/2016 | Andino et al. |
| 2016/0144105 | A1 | 5/2016 | Hooven et al. |
| 2017/0092101 | A1 | 3/2017 | Edwards et al. |
| 2017/0136183 | A1 | 5/2017 | Helmer |

FOREIGN PATENT DOCUMENTS

| | | | | |
|---|---|---|---|---|
| WO | WO-2012032411 | A2 | 3/2012 | |
| WO | WO-2013140395 | A1 | 9/2013 | |
| WO | WO-2016053954 | A1 | 4/2016 | |
| WO | WO-2016172182 | A1 * | 10/2016 | ........ A61M 5/14248 |
| WO | WO-2017007952 | A1 * | 1/2017 | ........ A61M 5/14248 |

OTHER PUBLICATIONS

Written Opinion for International Application No. PCT/US2018/021126, dated Jun. 6, 2018.
Japanese Patent Application No. 2019-548357, Notice of Rejection, dated Aug. 17, 2021.
European Patent Application No. 18712758.4, Communication Pursuant to Article 94(3) EPC, dated Jan. 12, 2023.

* cited by examiner

DRUG DELIVERY DEVICE WITH ACTIVATION PREVENTION FEATURE

CROSS-REFERENCE TO RELATED APPLICATIONS

This is the United States National Phase of PCT/US18/21126, filed Mar. 6, 2018, which claims the priority benefit of U.S. Provisional Patent Application No. 62/467,602, filed Mar. 6, 2017, the entire contents of each of which are hereby incorporated by reference herein.

FIELD OF THE DISCLOSURE

The present disclosure generally relates to drug delivery devices and, more particularly, to drug delivery devices with manually depressible activator mechanisms.

BACKGROUND

Parenteral delivery of various drugs, i.e., delivery by means other than through the digestive tract, has become a desired method of drug delivery for a number of reasons. This form of drug delivery by injection may enhance the effect of the substance being delivered and ensure that the unaltered medicine reaches its intended site at a significant concentration. Similarly, it is also possible with parenteral delivery to avoid undesirable side effects such as systemic toxicity associated with other routes of delivery. By bypassing the digestive system of a mammalian patient, one can avoid degradation of the active ingredients caused by the catalytic enzymes in the digestive tract and liver and ensure that a necessary amount of drug, at a desired concentration, reaches the targeted site.

Traditionally, manual syringes and injection pens have been employed for delivering parenteral drugs to a patient. More recently, parenteral delivery of liquid medicines into the body has been accomplished by administering bolus injections using a needle and reservoir, continuously by gravity driven dispensers, or via transdermal patch technologies. Bolus injections can require large individual doses. Continuous delivery of medicine through gravity-feed systems can compromise the patient's mobility and lifestyle, and limit therapy to simplistic flow rates and profiles. Transdermal patches often require specific molecular drug structures for efficacy, and the control of the drug administration through a transdermal patch can be severely limited.

In recent years, wearable drug delivery devices, which are sometimes referred to as on-body injectors, have grown in applicability and preference. Like syringes, these wearable devices deliver drug by inserting a needle or cannula into the patient. But, unlike conventional syringes and pens, the patient or caregiver is not required to interact with the device after it is placed onto the patient's skin and activated. For some patients, this removes the fear associated with manually inserting a needle or depressing a syringe plunger. Regardless, for those devices that include externally located and manually operable activator mechanisms, the process of placing the device on the patient's skin must be performed with a certain level of care to avoid inadvertent activation.

SUMMARY

One aspect of the present disclosure provides a wearable drug delivery device including a housing, a reservoir, a needle or cannula, a drive mechanism, an activator mechanism, and an activation prevention mechanism. The reservoir is adapted to store a drug product. The needle or cannula is in fluid communication with the reservoir. The drive mechanism is for selectively urging the drug product out of the reservoir, through the needle or cannula and to a patient. The activator mechanism is disposed on an external surface of the housing for enabling a user to activate the drive mechanism. Finally, the activation prevention mechanism is removably coupled to the housing and/or the activator mechanism to prevent inadvertent actuation of the activator mechanism.

In some aspects, the activator mechanism includes a manually depressible activator button operably coupled to the drive mechanism, and the activation prevention mechanism includes a coupling portion that is removably coupled to the activator button between the activator button and the housing to prevent the activator button from being depressed to activate the drive mechanism.

In some aspects, the activator mechanism further includes an activator stem connected between the button and the drive mechanism. And the activation prevention mechanism includes a plurality of forks defining a gap dimensioned to accommodate the stem such that the forks reside between the button and the housing to prevent actuation.

In some aspects, the activation prevention mechanism includes a securing portion engaging the housing for proper positioning of the activation prevention mechanism and/or for securing the activation prevention mechanism to the housing.

In some aspects, the securing portion includes a tab with a surface contoured to corresponding with a corresponding surface of the housing.

In some aspects, the activator mechanism includes a manually depressible activator button operably coupled to the drive mechanism, and the activation prevention mechanism includes a shell portion at least partially enclosing the activator button to prevent inadvertent manipulation of the activator mechanism.

In some aspects, shell portion of the activation prevention mechanism is at least one of: (a) transparent, (b) translucent, (c) opaque, (d) rigid, and (e) more rigid than the remainder of the activation prevention mechanism.

In some aspects, the activator mechanism includes an adhesive removably securing the activation prevention mechanism to the housing.

In some aspects, the shell portion is dimensioned to frictionally engage the activator button.

In some aspects, the activation prevention mechanism comprises a gripping portion for selectively removing the activation prevention mechanism from the injector housing.

In some aspects, the gripping portion of the activation prevention mechanism includes an integral tab comprising either (a) a rigid tab, or (b) a flexible tab.

In some aspects, the activation prevention mechanism includes a gripping portion for selectively removing the activation prevention mechanism from the injector housing and a connecting portion disposed between the shell portion and the gripping portion.

In some aspects, the activator mechanism includes a manually depressible activator button operably coupled to the drive mechanism, and the activation prevention mechanism includes a frame portion at least partially enclosing the activator button to prevent inadvertent manipulation of the activator mechanism. In further aspects, the frame portion can include a front wall portion and lateral side prongs that define a chamber sized to receive the activator button therein. In yet further aspects, at least one of the front wall portion or the lateral side portions can include catches that extend along opposite sides of the activator button to hold the frame portion on the activator button.

In some aspects, the activator mechanism further includes an activator stem connected between the activator button and the drive mechanism, and the activation prevention mechanism includes an opening extending therethrough with an insertion portion and coupling portion. The insertion portion is sized to receive the activator button therethrough and the coupling portion is sized so that the activator stem can pass, but has a dimension smaller than the activator button.

In some aspects, the activator mechanism further includes an activator stem connected between the activator button and the drive mechanism, where the activator stem including an opening extending therethrough, and the activation prevention mechanism includes an insertion portion sized to be inserted into the opening of the activator stem. In further aspects, the activation prevention mechanism can include a flexible intermediate portion adjacent to the insertion portion.

Another aspect of the present disclosure provides a wearable drug delivery device, including a housing, a reservoir, a needle or cannula, a drive mechanism, an activator mechanism and an activation prevention mechanism. The reservoir is adapted to store a drug product. The needle or cannula is in fluid communication with the reservoir. The drive mechanism is for selectively urging the drug product out of the reservoir, through the needle or cannula and to a patient. The activator mechanism is disposed on an external surface of the housing for enabling a user to activate the drive mechanism. The activator mechanism includes a manually depressible activator button operably coupled to the drive mechanism. Finally, the activation prevention mechanism is removably coupled to the activator mechanism between the activator button and the housing to prevent the activator button from being depressed to activate the drive mechanism.

In some aspects, the activator mechanism further includes an activator stem connected between the button and the drive mechanism, and the activation prevention mechanism includes a plurality of forks defining a gap dimensioned to accommodate the stem such that the forks are adapted to reside between the button and the housing to prevent actuation.

In some aspects, the activation prevention mechanism includes a securing portion adapted to engage the housing for proper positioning of the activation prevention mechanism and/or for securing the activation prevention mechanism to the housing.

In some aspects, the securing portion includes a tab with a surface contoured to engage a corresponding surface of the housing.

In some aspects, the activation prevention mechanism comprises a gripping portion for selectively removing the activation prevention mechanism from the injector housing.

In some aspects, the gripping portion of the activation prevention mechanism includes a rigid integral tab.

Yet another aspect of the present disclosure provides a wearable drug delivery device, including a housing, a reservoir, a needle or cannula, a drive mechanism, an activator mechanism, and an activation prevention mechanism. The reservoir is adapted to store a drug product. The needle or cannula is in fluid communication with the reservoir. The drive mechanism is for selectively urging the drug product out of the reservoir, through the needle or cannula and to a patient. The activator mechanism disposed on an external surface of the housing for enabling a user to activate the drive mechanism and including a manually depressible activator button operably coupled to the drive mechanism. Finally, the activation prevention mechanism is removably coupled to the housing to prevent inadvertent actuation of the activator mechanism, the activation prevention mechanism comprising a shell portion at least partially enclosing the activator button.

In some aspects, the shell portion of the activation prevention mechanism is at least one of: (a) transparent, (b) translucent, (c) opaque, (d) rigid, and (e) more rigid than the remainder of the activation prevention mechanism.

In some aspects, the activator mechanism includes an adhesive removably securing the activation prevention mechanism to the housing.

In some aspects, the shell portion is dimensioned to frictionally engage the activator button.

In some aspects, the activation prevention mechanism comprises a gripping portion for selectively removing the activation prevention mechanism from the injector housing.

In some aspects, the gripping portion of the activation prevention mechanism includes an integral flexible tab.

In some aspects, the activation prevention mechanism includes a connecting portion disposed between the shell portion and the gripping portion.

In some aspects, the reservoir of the wearable drug delivery device of the present disclosure is filled with a drug product.

The present disclosure also provides a method for allowing operation of a drug delivery device that includes grasping a gripping portion of an activation prevention mechanism that is removably coupled to a housing of the drug delivery device and/or an activator mechanism of the drug delivery device disposed on an external surface of the housing, where the activator mechanism prevents inadvertent actuation of the activator mechanism. The method further includes pulling the activation prevention mechanism away from the housing and/or activator mechanism to decouple the activation prevention mechanism therefrom.

In some aspects, pulling the activation prevention mechanism away from the housing and/or activator mechanism can include one or more of: pulling the activation prevention mechanism away from the activator mechanism so that forks of the activation prevent mechanism resiliently deform and allow a stem of the activator mechanism to pass between the forks; pulling the activation prevention mechanism away from the activator mechanism to pull an insertion portion of the activation prevention mechanism out of an opening extending through a stem of the activation prevention mechanism; sliding the activation prevention mechanism along a surface of the housing so that an activator button of the activator mechanism aligns with an insertion portion of an opening of the activation prevention mechanism and pulling the activation prevention mechanism away from the activator mechanism so that the activator button pass through the insertion portion of the opening; pulling a shell portion of the activation prevention mechanism that at least partially encloses an activator button of the activator mechanism away from the activator mechanism; or pulling a frame portion of the activation prevention mechanism that includes a front wall and lateral side prongs that at least partially enclose an activator button of the activator mechanism away from the activator mechanism.

In some aspects, pulling the activation prevention mechanism away from the housing and/or activator mechanism can include peeling an adhesive disposed between the activation prevention mechanism and the housing.

In some aspects, the method can further include actuating the activator mechanism to operate the drug delivery device.

The present disclosure further provides a method for preventing operation of a drug delivery device that includes grasping a gripping portion of an activation prevention mechanism and coupling the activation prevention mechanism to a housing of the drug delivery device and/or an activator mechanism of the drug delivery device disposed on an external surface of the housing, so that the activation prevention mechanism prevents inadvertent actuation of the activator mechanism.

In some aspects, coupling the activation prevention mechanism to the housing of the drug delivery device and/or the activator mechanism of the drug delivery can include one or more of: pushing the activation prevention mechanism toward the activator mechanism so that forks of the activation prevent mechanism resiliently deform and allow a stem of the activator mechanism to pass between the forks; inserting a portion of the activation prevention mechanism into an opening extending through a stem of the activation prevention mechanism; inserting an activator button of the activator mechanism through an insertion portion of an opening extending through the activation prevention mechanism and sliding the activation prevention mechanism along a surface of the housing so that a stem of the activator mechanism slides into a coupling portion of the opening, the coupling portion of the opening having a dimension smaller than a corresponding dimension of the activator button; mounting a shell portion of the activation prevention mechanism to the housing and/or activator mechanism so that the shell portion at least partially encloses an activator button of the activator mechanism; or mounting a frame portion of the activation prevention mechanism that includes a front wall and lateral side prongs to an activator button of the activator mechanism so that the frame portion at least partially encloses the activator button.

In some aspects, the method can further include adhering a portion of the activation prevention mechanism to the housing and/or activator mechanism.

BRIEF DESCRIPTION OF THE DRAWINGS

The drug delivery device of the present disclosure will be understood in view of the following detailed description, particularly when studied in conjunction with the drawings, wherein.

Figure 1:
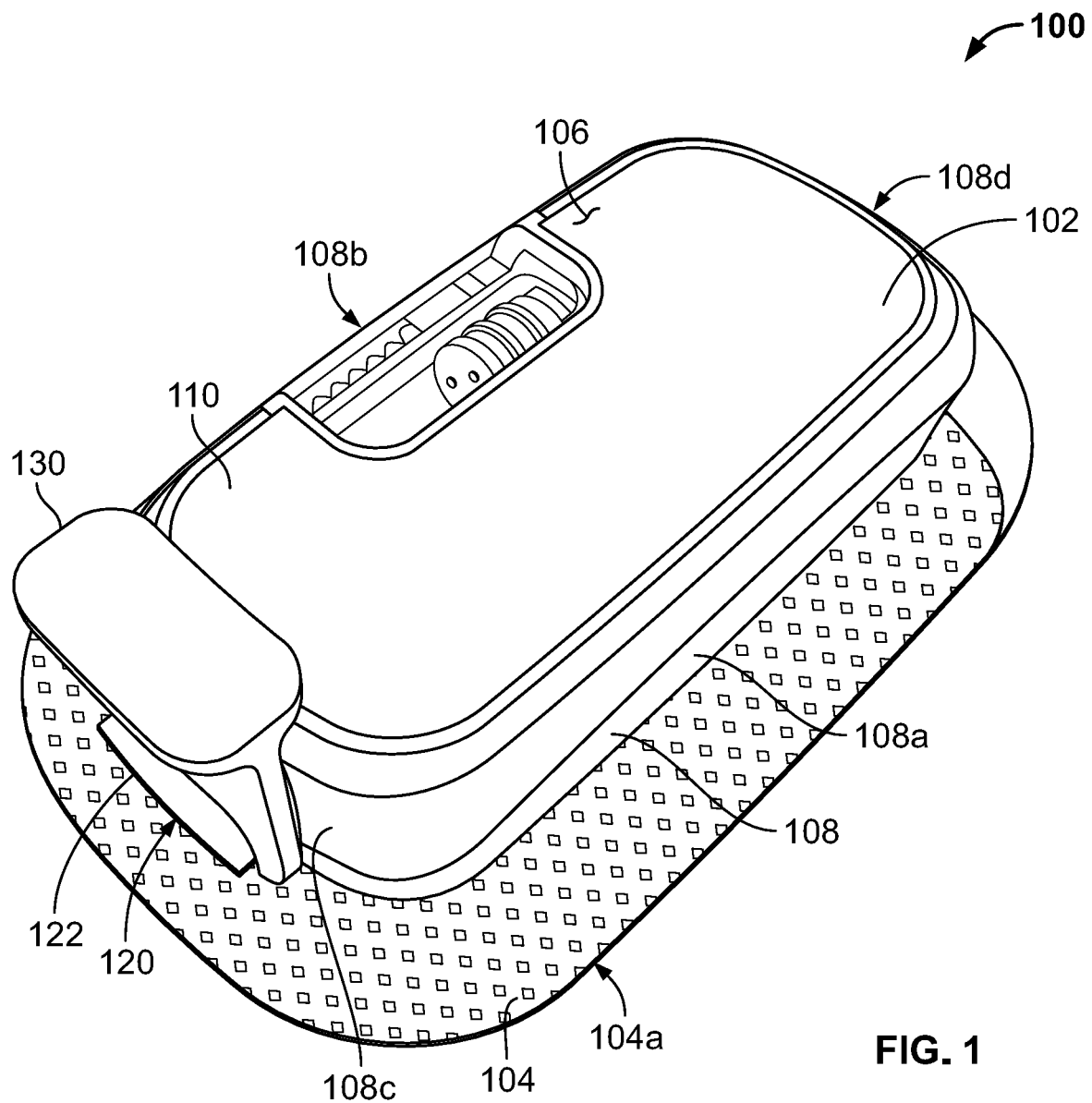
FIG. 1 is a perspective view of a first embodiment of an on-body injector with an activation prevention mechanism in accordance with the present disclosure.

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments. It will further be appreciated that certain actions and/or steps may be described or depicted in a particular order of occurrence while those skilled in the art will understand that such specificity with respect to sequence is not actually required. It will also be understood that the terms and expressions used herein have the ordinary technical meaning as is accorded to such terms and expressions by persons skilled in the technical field as set forth above except where different specific meanings have otherwise been set forth herein.

DETAILED DESCRIPTION

Wearable injectors, which are often referred to as on-body injectors, can be applied to a patient's skin with an adhesive applicator. Selecting the configuration of the applicator requires consideration of at least the following two events: (1) applying the injector to the patient's skin and (2) removing the injector from the patient's skin. Each event includes different circumstances. For example, application may require a user to remove an adhesive backing layer to expose the adhesive layer, and then subsequently place the device against the skin with sufficient force to ensure a strong bond. Additionally, during application, it is important that the adhesive layer does not fold onto itself thereby rendering a portion of the adhesive layer unusable. This can be critical in situations where the injector includes a pre-filled injector because if the adhesive layer becomes unusable, the entire injector including the drug product in the injector may have to be discarded. Alternatively, the removal process requires some level of strength and dexterity to break the adhesive bond with the patient's skin. Moreover, a patient may wish to first affix the device to their skin and administer the drug at a later time. During the application process and/or during the period between affixing the injector and administering the drug, the patient may accidentally come into contact with the device (e.g., by accidentally bumping the device), which may in turn accidentally activate the device and administer the drug prior to the desired time. As such, disclosed herein are various novel arrangements for preventing inadvertent activation of the device.

FIGS. 1-4 depict a first embodiment of an on-body drug delivery device 100 including an injector 102, an adhesive applicator 104, an activator mechanism 120, and an activation prevention mechanism 130. The injector 102 can include a pre-filled, pre-loaded drug delivery device having an external housing 106 that includes a number of sidewalls 108a, 108b, 108c, 108d and a generally planar outer or top surface 110. As is generally known, the housing can contain, for example, a drug reservoir filled (or adapted to be filled) with a drug, a needle and/or a cannula for insertion into a patient, and a drive mechanism for urging the drug out of the reservoir and into the patient as is generally known in the art. As shown, the injector 102 of this embodiment can include any number of additional features such as side grips molded into a side wall 108 of the housing 106 for assisting a user with grasping the device 100 for placement and/or removal. As an example, side grips can include elongated recesses molded into the housing 106 at a location between the bottom and the top surface 110 of the housing 106. The adhesive applicator 104 of this embodiment can include a non-woven material fixed to a bottom surface of the injector 102 and includes a dimension that is larger than the injector 102. So configured, the adhesive applicator 104 includes a perimeter portion 104a that encircles the injector 102. A bottom surface of the adhesive applicator 104 includes a layer of an adhesive (not shown) and an adhesive backing material (not shown).

So configured, to apply and use the device 100, a user must first remove the adhesive backing layer to expose the adhesive layer. Then, the entire device can be placed against a patient's injector site such that exposed adhesive on the adhesive applicator 104 adheres to the patient's skin. The user then activates the activator mechanism 120, which causes the drive mechanism to urge the drug product out of the reservoir, through the needle or cannula, and to the patient. After injection, a user can simply peel the perimeter portion 104a of the adhesive applicator 104 away from the skin with one hand, while grasping the injector 102 at the side grips with the other hand and pulling away from the patient.

The activator mechanism 120 includes a manually operable activator button 122 and an activator stem (not shown) is coupled and/or fixed to the activator button 122. The activator stem is disposed through an opening (not shown) of the sidewall 108c and is operably coupled to the drive mechanism. A portion of the activator stem extends outwardly beyond the sidewall 108c in order to allow the activator button 122 to be depressed inwardly toward the housing 106 in order to actuate the device.

The activation prevention mechanism 130 of this embodiment is operably coupled to the housing 106 and/or the activator mechanism 120 to prevent the activator mechanism 120 from being inadvertently actuated (e.g., depressed). The activation prevention mechanism 130 includes a body 132 having a gripping portion 134 for selectively handling the activation prevention mechanism 130, e.g., for removing the mechanism 130 from the housing 106 and for coupling the activation prevention mechanism 130 to the injector housing 106. The gripping portion 134 may include a first surface 134a, a second surface 134b, and a third surface 134c. In the illustrated example, the first surface 134a is a generally flat surface, and the second and third surfaces 134b, 134c are both generally curved surfaces. The third surface 134c may be curved and/or shaped to correspond to the shape of the sidewall 108. When the activation prevention mechanism 130 is coupled to the housing 106, the gripping portion 134 protrudes outwardly from the top surface 110 to allow a user to grasp the gripping surfaces 134a, 134b, 134c in order to remove the activation prevention mechanism 130 from the device 100.

Figure 3:
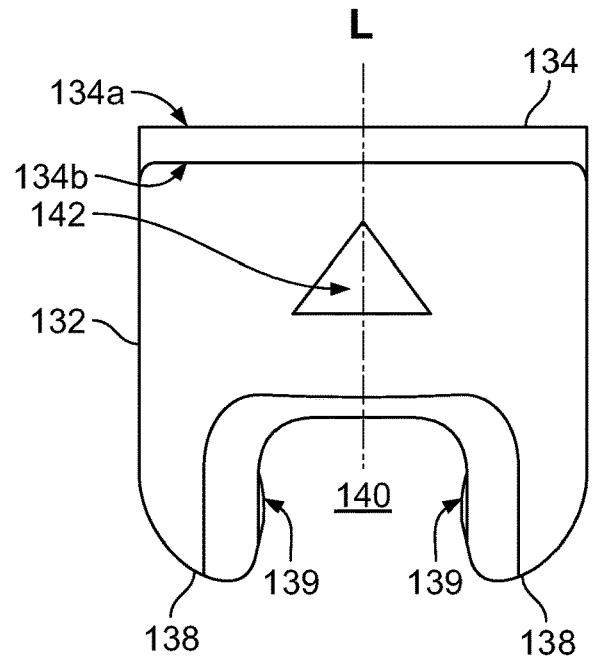
FIG. 3 is a top plan view of the activation prevention mechanism of FIGS. 1 and 2.

The activation prevention mechanism 130 further includes a coupling portion 136 that includes forks 138 and gap or opening 140. The forks 138 may be of any shape and/or dimension that generally correspond to a cross sectional shape and dimension of the activator stem. The coupling portion 136 (as well as the entirety of the activation prevention mechanism 130) may be constructed from a resilient material capable of slightly deforming when a force is applied thereto, or may be completely rigid. As illustrated in FIG. 3, the forks 138 are generally symmetrical about axis L and include catches 139 that protrude inwardly towards axis L. These catches 139 engage the activator stem in order to increase the force required to remove the activation prevention mechanism 130 from the device 100.

The device 100 may be provided to patients with the activation prevention mechanism 130 already coupled thereto. However, to couple the activation prevention mechanism 130 to the device, a user may align the gap 140 with the activator stem and press downwardly on the first surface 134a. In one version, the forks 138 may slightly deform outwardly (i.e., in a direction away from axis L) until the activator stem has cleared the catches 139 and is nested in the gap 140. In other versions, forks 138 do not deform but the user applied force must merely overcome a frictional force between the catches 139 and the stem. Upon the activator stem clearing the catches 139, the forks 138 may return to an original resting configuration.

So configured, the legs 138 at least partially surround the activator stem, and the legs 138 remain in contact with the activator button 122. Also, the forks 138 reside between the button 122 and the housing 106 thereby acting as an interference that prevents the button 122 from being depressed and moving toward the housing 106. Said another way, when the activation prevention mechanism 130 is coupled to the device 100, a patient will not be able to intentionally or unintentionally depress the activator button 122 to actuate the device because the motion of travel is obstructed by the forks 138.

Figure 2:
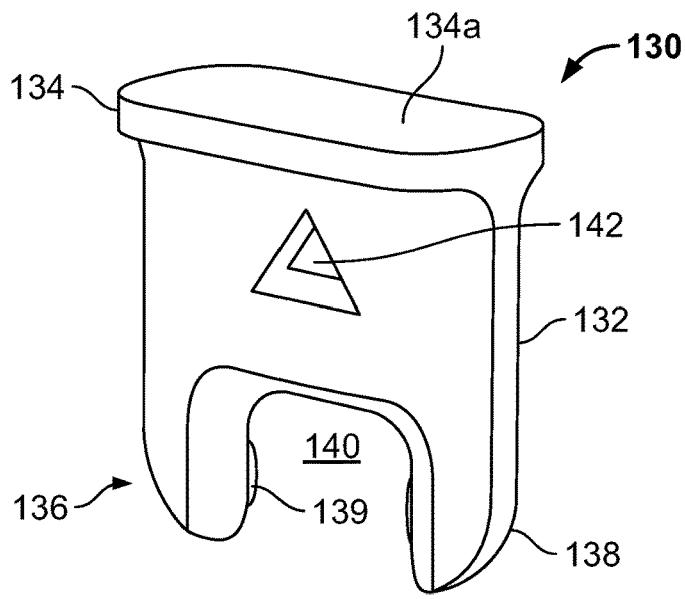
FIG. 2 is a perspective view of the activation prevention mechanism of FIG. 1.

To remove the activation prevention mechanism 130 from the device 100, a user may grasp the gripping portion and pull the activation prevention mechanism 130 upwardly and away from the device 100. As illustrated in FIGS. 2 and 3, the activation prevention mechanism 130 may include an indicator 142 (e.g., an arrow formed in the body 132) to assist in identifying the direction to pull the activation prevention mechanism 130. Upon pulling the activation prevention mechanism 130, the forks 138 may again slightly deform to allow the activator stem to clear the catches 139.

Figure 4:
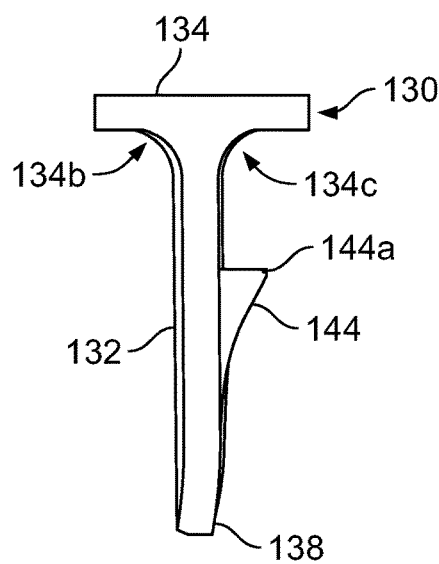
FIG. 4 is a right side elevation view of the activation prevention mechanism of FIGS. 1-3.

In some examples, and as illustrated in FIG. 4, the activation prevention mechanism 130 may also include a securing portion 144 to secure the activation prevention mechanism 130 to the housing 106. In the illustrated example, the securing portion 144 is a tab that engages the sidewall 108c or in some versions a groove (not shown) formed by and/or disposed on the sidewall 108c. An upper surface 144a of the tab may engage a surface of the groove to further restrict the activation prevention mechanism 130 from being removed from the device 100. Other examples of securing portions 144 are possible.

Figure 5:
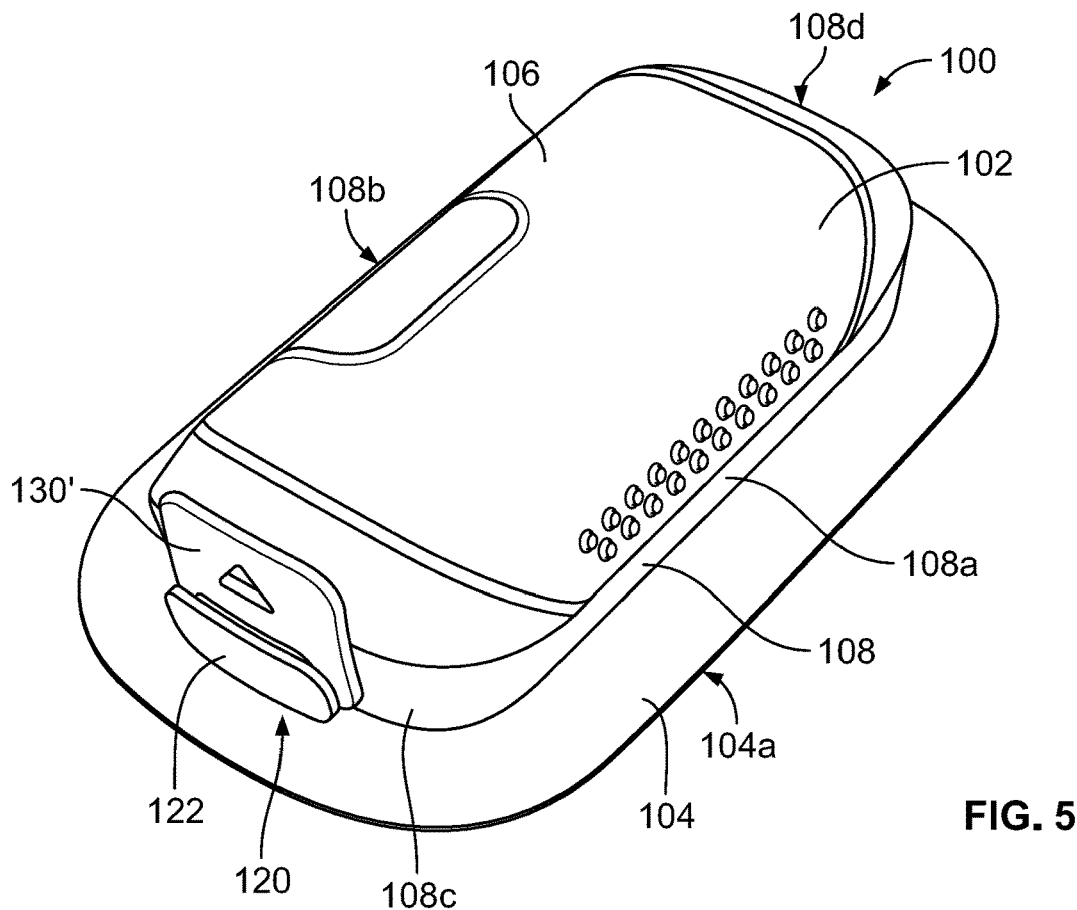
FIG. 5 is a perspective view of a second embodiment of an on-body injector with an activation prevention mechanism in accordance with the present disclosure.
Figure 6:
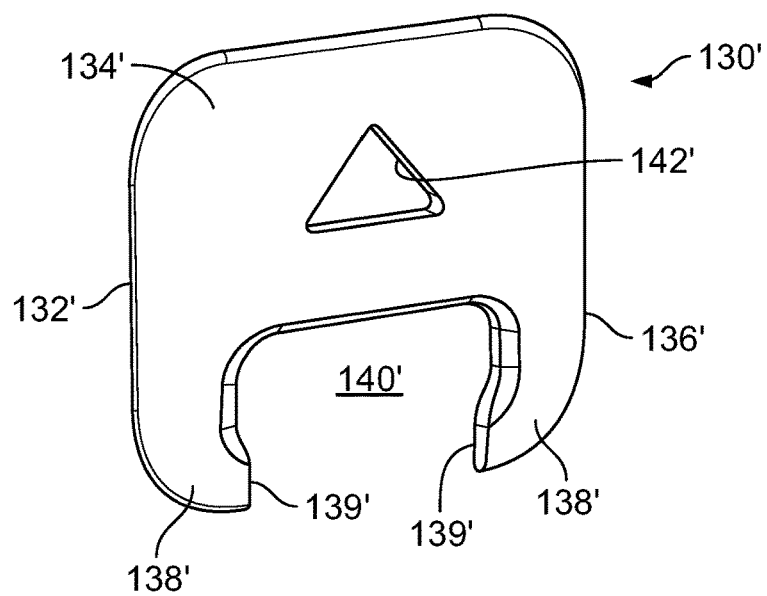
FIG. 6 is a perspective view of the activation prevention mechanism of FIG. 5.

Another embodiment is shown in FIGS. 5 and 6 that includes an activation prevention mechanism 130' with a form similar to the mechanism 130 of FIGS. 1-4 without an outwardly projecting gripping portion 134. Instead, as illustrated, the mechanism 130 includes a planar tab gripping portion 134'. The mechanism 130' includes a body 132' with a coupling portion 136' having forks 138' configured similarly to the above form. The body 132' further includes an indicator 142' that may be a through opening as shown, a recess, or a projection providing tactile edges or surfaces.

With this configuration, a user can press the mechanism 130' downwardly onto the activator stem and the forks 138' at least partially surround the activator stem and remain in contact with the activator button 122. Also, the forks 138' reside between the button 122 and the housing 106 thereby acting as an interference that prevents the button 122 from being depressed and moving toward the housing 106. Said another way, when the activation prevention mechanism 130' is coupled to the device 100, a patient will not be able to intentionally or unintentionally depress the activator button 122 to actuate the device because the motion of travel is obstructed by the forks 138'. Further, when activation is desired, a user can grip the body 132' and pull upwardly to deflect the forks 138' and disengage the mechanism 130' from the activator stem. The tactile edges and/or opening of the indicator 142' can provide gripping surfaces for the user to easily remove the mechanism 130' from the device 100.

Figure 7:
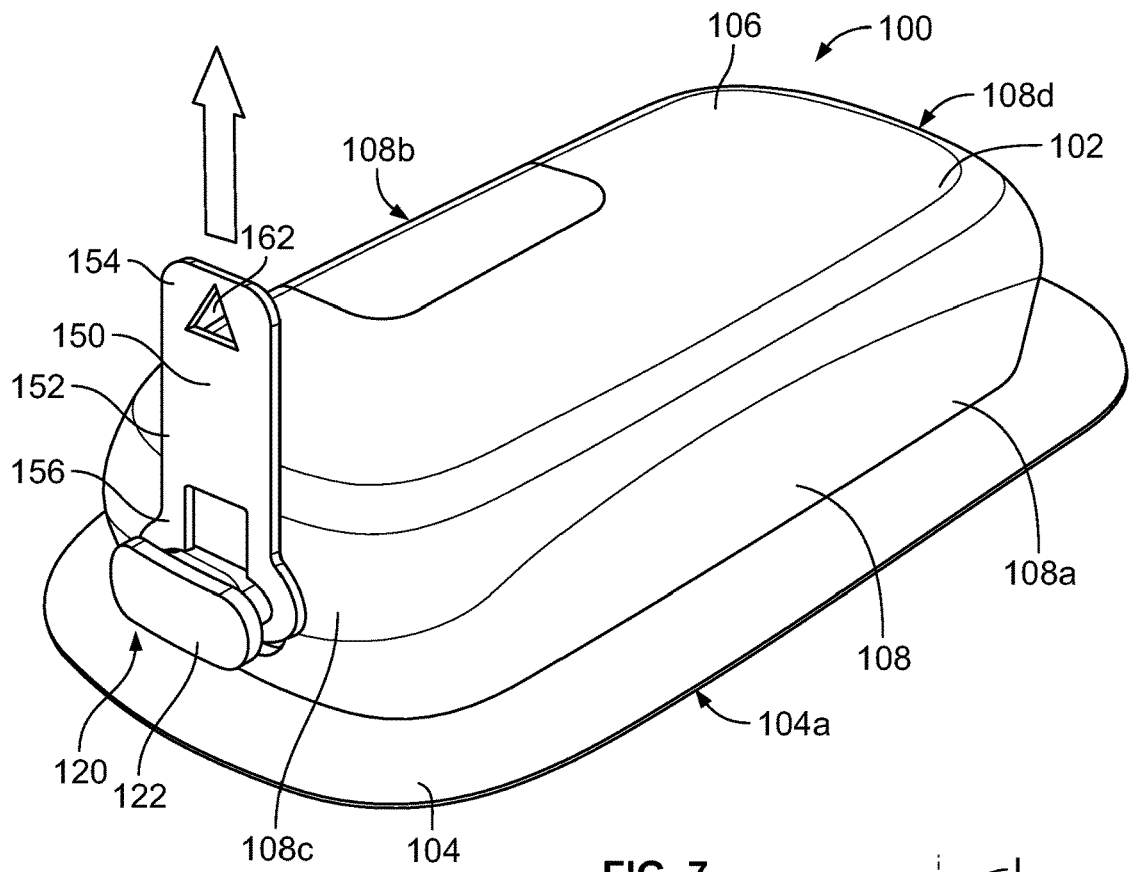
FIG. 7 is a perspective view of a third embodiment of an on-body injector with an activation prevention mechanism in accordance with the present disclosure.
Figure 8:
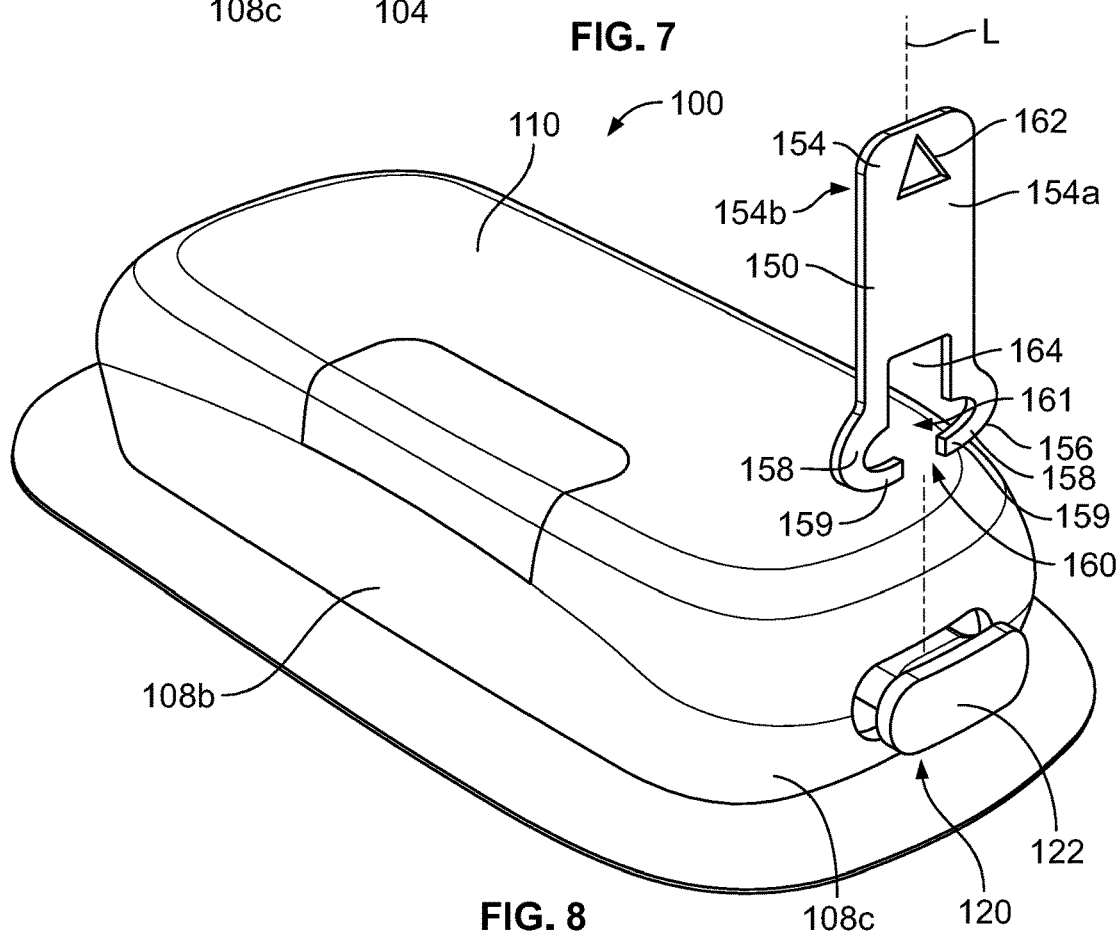
FIG. 8 is a perspective view of the on-body injector and the activation prevention mechanism of FIG. 7 uncoupled from one another.
Figure 9:
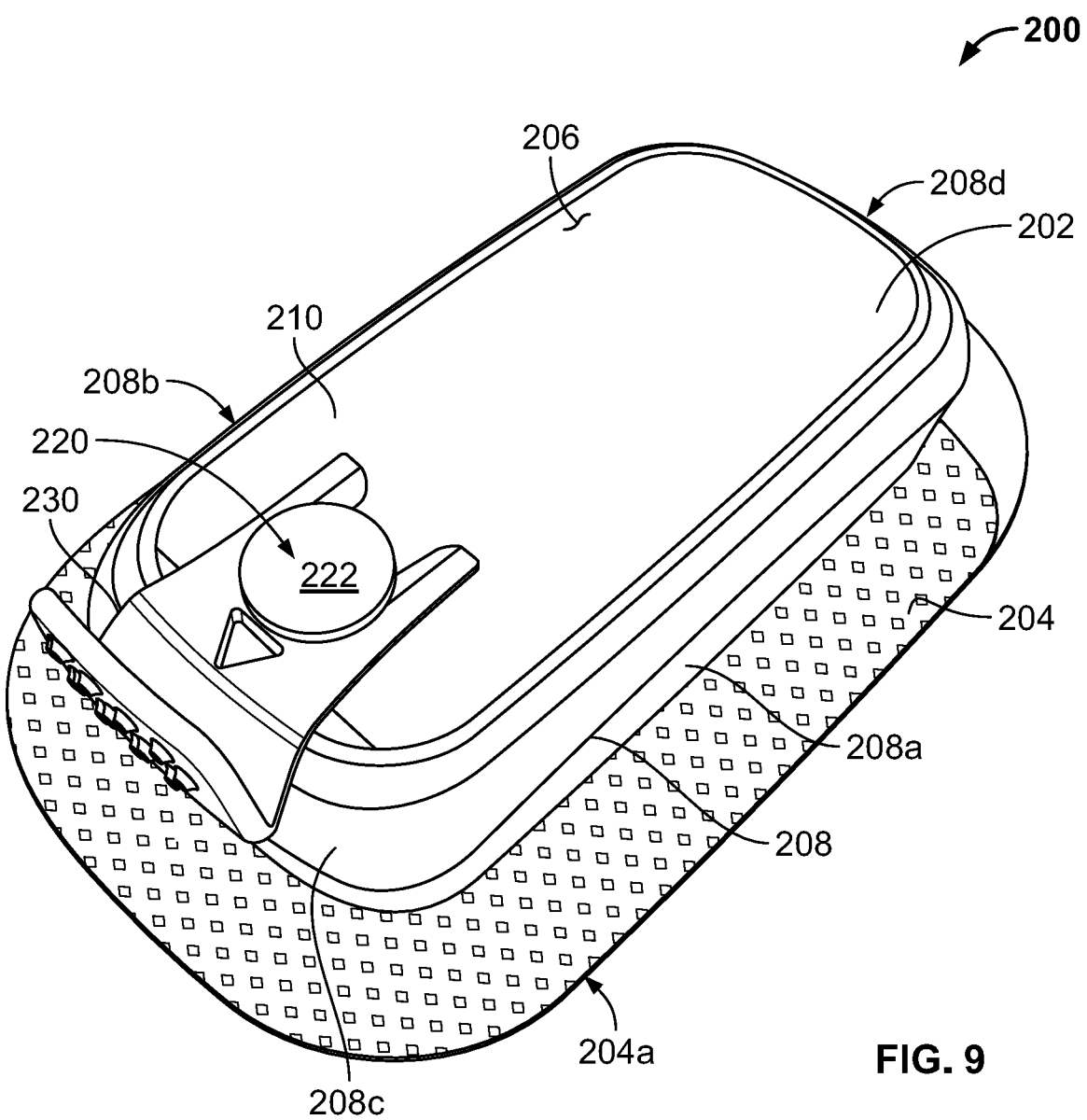
FIG. 9 is a perspective view of a fourth embodiment of an on-body injector with an activation prevention mechanism in accordance with the present disclosure.

A third embodiment is shown in FIGS. 7 and 8. In this form, an activation prevention mechanism 150 operably couples to the activator mechanism 120 of the device 100 to prevent the activator mechanism 120 from being inadvertently actuated (e.g., depressed). The activation prevention mechanism 150 includes a body 152 with a planar configuration. The body 152 includes an upper gripping portion 154 for selectively handling the activation prevention mechanism 150, e.g., for removing the mechanism 150 from the housing 106 and for coupling the mechanism 150 to the housing 106. The gripping portion 154 includes opposite first and second surfaces 154a, 154b. When the activation prevention mechanism 150 is coupled to the housing 106, the gripping portion 154 protrudes outwardly from the top surface 110 to allow a user to grasp the gripping surfaces 154a, 154b in order to remove the activation prevention mechanism 150 from the device 100. The gripping portion 154 can further include an indicator 162 (e.g., an arrow formed in the body 152) to assist in identifying the direction to pull the activation prevention mechanism 150. The indicator 162 may be a through opening as shown, a recess, or a projection providing tactile edges or surfaces for a user to get a better grip on the gripping portion 154.

The activation prevention mechanism 150 further includes a coupling portion 156 that includes prongs 158 defining a coupling area 161 therebetween and a gap or opening 160 at a bottom thereof. The coupling area 161 may be of any shape and/or dimension that generally corresponds to a cross sectional shape and dimension of the activator stem. The coupling portion 156 (as well as the entirety of the activation prevention mechanism 150) may be constructed from a resilient material capable of slightly deforming when a force is applied thereto, or may be completely rigid. As illustrated in FIG. 8, the prongs 158 are generally symmetrical about axis L and have an outwardly curved configuration with bottom catch portions 159 that protrude inwardly towards axis L. The catches 159 protrude underneath the activator stem in order to increase the force required to remove the activation prevention mechanism 150 from the device 100.

The device 100 may be provided to patients with the activation prevention mechanism 150 already coupled thereto. However, to couple the activation prevention mechanism 150 to the device 100, a user may align the gap 160 with the activator stem and press downwardly. The prongs 158 may deform outwardly (i.e., in a direction away from axis L) until the activator stem has cleared the catches 159 and is nested in the coupling area 161. To provide a greater flexibility for the prongs 158, the mechanism 150 can include an additional gap or opening 164 between the prongs 158 above the coupling area 161. Upon the activator stem clearing the catches 159, the prongs 158 may resiliently return to an original resting configuration extending around the stem.

So configured, the prongs 158 at least partially surround the activator stem and remain in contact with the activator button 122. Also, the prongs 158 reside between the button 122 and the housing 106 thereby acting as an interference that prevents the button 122 from being depressed and moving toward the housing 106. Said another way, when the activation prevention mechanism 150 is coupled to the device 100, a patient will not be able to intentionally or unintentionally depress the activator button 122 to actuate the device because the motion of travel is obstructed by the prongs 158.

To remove the activation prevention mechanism 150 from the device 100, a user may grasp the gripping portion 154 and pull the activation prevention mechanism 150 upwardly and away from the device 100. Upon pulling the activation prevention mechanism 150, the prongs 158 may again slightly deform to allow the activator stem to clear the catches 159.

FIGS. 9-12 depict a fourth embodiment of an on-body drug delivery device 200. It is understood that the device 200 includes similar features and components as the device 100 described with reference to FIGS. 1-8, thus reference numerals having identical two-digit suffixes (e.g., injector 202, adhesive applicator 204, and the like) have similar construction and operation as corresponding components in the device 100. It is understood that features described with regard to the device 100 and/or 200 can be used interchangeably in either of these embodiments. The device 200 includes an activator mechanism 220 and an activation prevention mechanism 230. The injector 202 can include a pre-filled, pre-loaded drug delivery device having an external housing 206 that includes a number of sidewalls 208a, 208b, 208c, 208d and a generally planar outer or top surface 210. The housing can contain, for example, a drug reservoir filled (or adapted to be filled) with a drug, a needle and/or a cannula for insertion into a patient, and a drive mechanism for urging the drug out of the reservoir and into the patient as is generally known in the art. The adhesive applicator 204 of this embodiment can include a non-woven material fixed to a bottom surface of the injector 202 and includes a dimension that is larger than the injector 202. So configured, the adhesive applicator 204 includes a perimeter portion 204a that encircles the injector 202. A bottom surface of the adhesive applicator 204 includes a layer of an adhesive (not shown) and an adhesive backing material (not shown).

In this example, the activator mechanism 220 includes an activator button 222 and an activator stem (not shown) coupled to the activator button 222. The activator stem is disposed through an opening (not shown) of the top surface 210 and is operably coupled to the drive mechanism. A portion of the activator stem extends outwardly beyond the top surface 210 in order to allow the activator button 222 to be depressed inwardly toward the housing 206 in order to administer the drug.

The activation prevention mechanism 230 is operably coupled to the housing 206 and/or the activator mechanism 220 to prevent the activator mechanism 220 from being inadvertently actuated. The activation prevention mechanism 230 includes a body 232 having a gripping portion 234 for selectively removing the activation prevention mechanism 230 from the housing 206 and for coupling the activation prevention mechanism 230 to the injector housing 206. The gripping portion 234 may include a first surface 234a, and a second surface 234b. In the illustrated example, the first and second surfaces 234a, 234b are generally flat and include gripping features 235 in the form of bumps or protrusions to assist in removing the activation prevention mechanism 230. Similar gripping features 235 can be utilized in any of the embodiments described herein. The body 232 includes a curved region 232a that is curved and/or shaped to correspond to the shape of the sidewall 208. When the activation prevention mechanism 230 is coupled to the housing 206, the gripping portion 234 protrudes outwardly from the housing 206 to allow a user to grasp the gripping surfaces 234a, 234b in order to remove the activation prevention mechanism 230 from the device 200.

Figure 11:
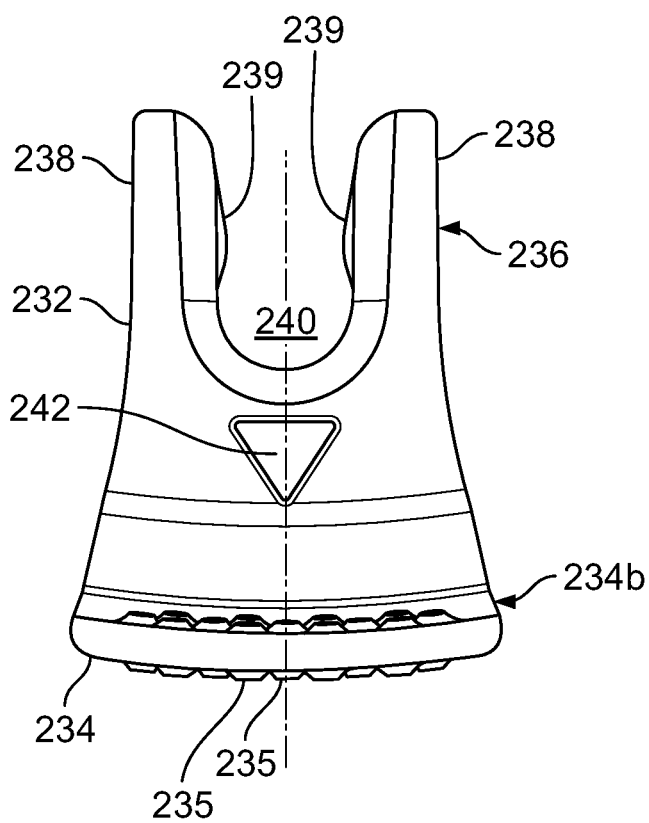
FIG. 11 is a top plan view of the activation prevention mechanism of FIGS. 9 and 10.
Figure 12:
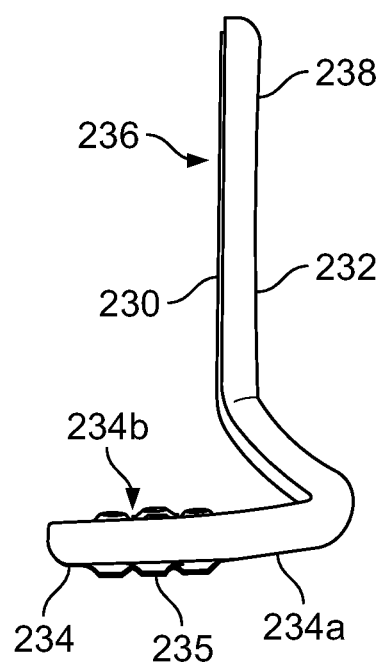
FIG. 12 is a right side elevation view of the activation prevention mechanism of FIGS. 9-11.

The activation prevention mechanism 230 further includes a coupling portion 236 that includes forks 238 that define a gap or opening 240 therebetween. The forks 238 may be of any shape and/or dimension so that the gap 240 generally corresponds to a cross sectional shape and dimension of the activator stem. In the illustrated form, the gap 240 has a generally rectangular configuration with a curved end to be complementary to a curved activator stem. The coupling portion 236 (as well as the entirety of the activation prevention mechanism 230) may be constructed from a resilient material capable of slightly deforming when a force is applied thereto. As illustrated in FIG. 11, the forks 238 are generally symmetrical about axis L and include catches 239 that protrude inwardly towards axis L. These catches 239 engage the activator stem in order to increase the force required to remove the activation prevention mechanism 230 from the device 200.

The device 200 may be provided to patients with the activation prevention mechanism 230 already coupled thereto. However, to couple the activation prevention mechanism 230 to the device, a user may align the gap 240 with the activator stem and press downwardly on the first surface 234a. The forks 238 may slightly deform outwardly (i.e., in a direction away from axis L) until the activator stem has cleared the catches 239 and is nested in the gap 240. Upon the activator stem clearing the catches 239, the forks 238 may return to an original resting configuration. Similar to the first embodiment, in other versions the forks 238 may not be deformable but rather a user applied force must merely overcome frictional resistance between the catches 239 and the stem of the activator mechanism 220.

So configured, the forks 238 at least partially surround the activator stem and reside at a location between the button 222 and the housing, and the forks 238 remain in contact with the activator button 222. When the activation prevention mechanism 230 is coupled to the device 200, a patient will not be able to intentionally or unintentionally depress the activator button 222 to actuate the device because the motion of travel is obstructed by the forks 238.

Figure 10:
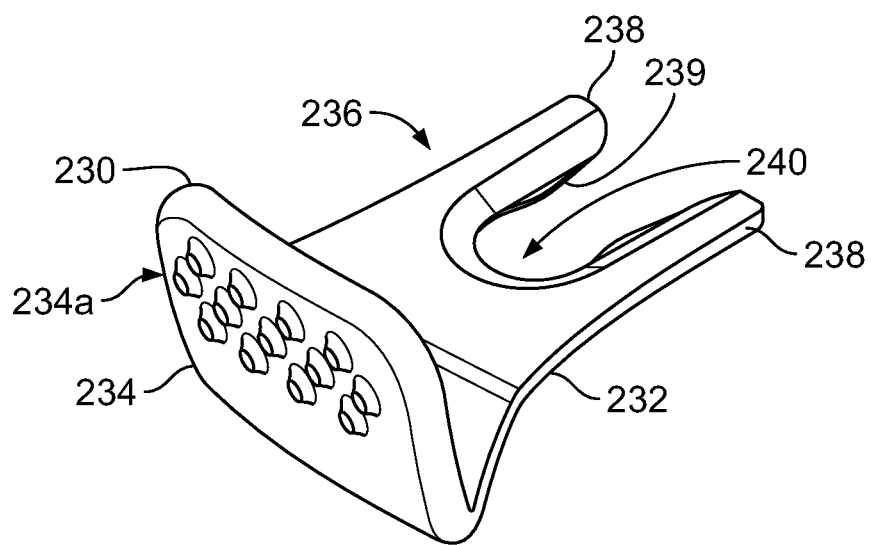
FIG. 10 is a is a perspective view of the activation prevention mechanism of FIG. 9.

To remove the activation prevention mechanism 230 from the device 200, a user may grasp the gripping portion and pull the activation prevention mechanism 230 away from the device 200. As illustrated in FIGS. 10 and 11, the activation prevention mechanism 230 may include an indicator 242 (e.g., an arrow formed in the body 232) to assist in identifying the direction to pull the activation prevention mechanism 230. Upon pulling the activation prevention mechanism 230, the forks 238 may again slightly deform (or friction must be overcome) to allow the activator stem to clear the catches 239.

Figure 13:
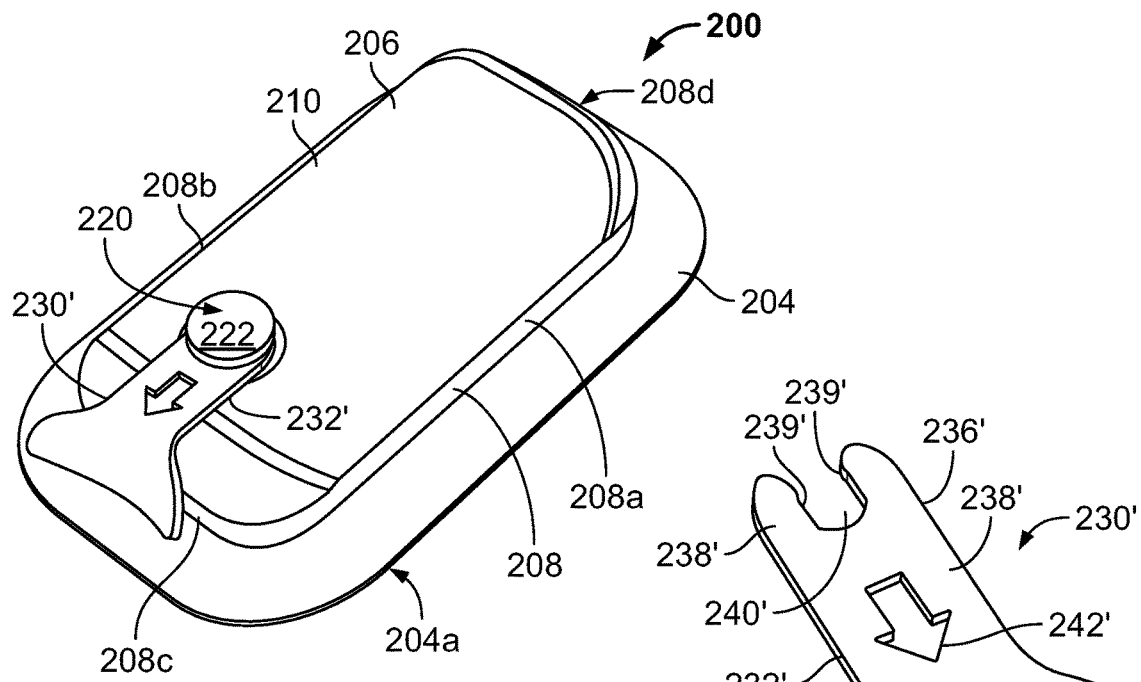
FIG. 13 is a perspective view of a fifth embodiment of an on-body injector with an activation prevention mechanism in accordance with the present disclosure.
Figure 14:
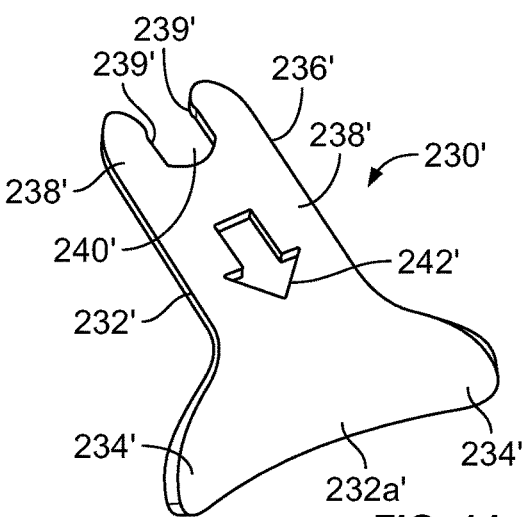
FIG. 14 is a perspective view of the activation prevention mechanism of FIG. 13.

A fifth embodiment is shown in FIGS. 13 and 14 that includes an activation prevention mechanism 230' with a form similar to the mechanism 230 of FIGS. 9-12 without an outwardly projecting gripping portion 234. Instead, as shown, the activation prevention mechanism 230' includes a body 232' with a curved region 232a' that is shaped to generally correspond to the curvature or shape of the sidewall 208. If desired, the body 232' can further include gripping portions 234' that project laterally outwardly from the curved region 232a'. The gripping portions 234' can curve or otherwise slant forwardly of the curved region 232a'. With this configuration, the gripping portions 234' project away from the housing 206 of the device 100 when the mechanism 230' is coupled thereto to allow a user to grasp the gripping portions 234' in order to remove the activation prevention mechanism 230' from the device 200.

The activation prevention mechanism 230' further includes a coupling portion 236' that includes forks 238' and a gap or opening 240' configured as described above. The forks 238' may be of any shape and/or dimension that generally corresponds to a cross sectional shape and dimension of the activator stem. The forks 238' can be generally symmetrical about axis L and include catches 239' that protrude inwardly towards axis L. Further, installation and removal of the activation prevention mechanism 230' can be performed similar to the above form 230, except that a user can grip the lateral gripping portions 234' rather than the gripping portion 234.

Figure 15:
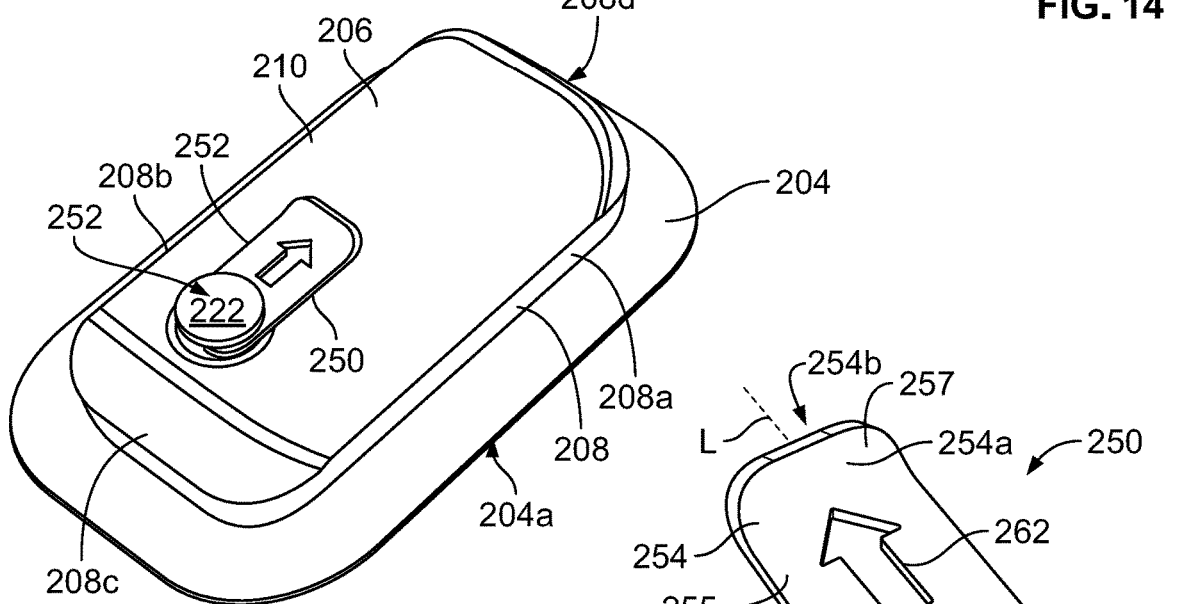
FIG. 15 is a perspective view of a sixth embodiment of an on-body injector with an activation prevention mechanism in accordance with the present disclosure.
Figure 16:
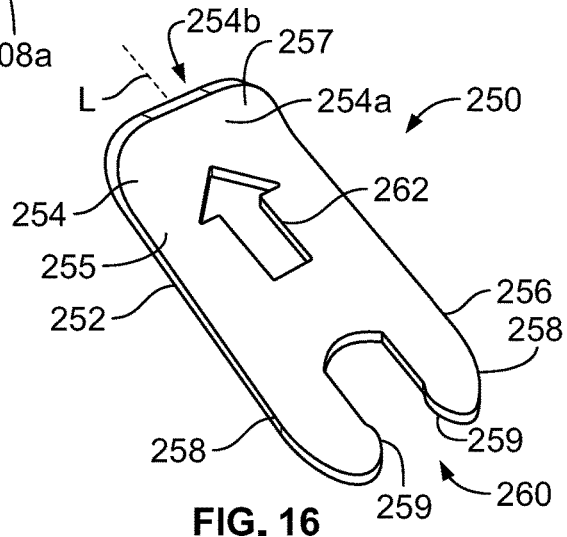
FIG. 16 is a perspective view of the activation prevention mechanism of FIG. 15.

A sixth embodiment of an activation prevention mechanism 250 is shown in FIGS. 15 and 16 that operably couples to the activator mechanism 220 of the device 200 to prevent the activator mechanism 220 from being inadvertently actuated (e.g., depressed). In this form, the mechanism 250 includes a body 252 that is configured to extend along the top surface 210 of the device 200 when installed to prevent activation of the device 200. The body 252 includes a gripping portion 254 that projects away from the top surface 210 so that the gripping portion 254 can be easily grasped by a user for selectively removing the activation prevention mechanism 250 from the housing 206 and for coupling the activation prevention mechanism 250 to the injector housing 206. The gripping portion 254 of the illustrated form includes opposing first and second surfaces 254a, 254b with a curved transition 255 from the remaining portion of the body 252 and a distal tab portion 257 that projects away from the remaining portion of the body 252.

The activation prevention mechanism 250 further includes a coupling portion 256 that includes forks 258 with a gap or opening 260 defined therebetween. The forks 258 may be of any shape and/or dimension that generally corresponds to a cross sectional shape and dimension of the activator stem. In the illustrated form, the gap 260 has a generally rectangular configuration with a curved end to be complementary to the activator stem. The coupling portion 236 (as well as the entirety of the activation prevention mechanism 250) may be constructed from a resilient material capable of slightly deforming when a force is applied thereto. As illustrated in FIG. 16, the forks 258 are generally symmetrical about axis L and include catches 259 that protrude inwardly towards axis L. These catches 259 engage the activator stem in order to increase the force required to remove the activation prevention mechanism 250 from the device 200.

The device 200 may be provided to patients with the activation prevention mechanism 250 already coupled thereto. However, to couple the activation prevention mechanism 250 to the device, a user may align the gap 260 with the activator stem and slide the mechanism 250 across the top surface 210. The user can then press the gripping portion 254 in a direction generally parallel to the top surface 210 and the forks 258 may slightly deform outwardly (i.e., in a direction away from axis L) until the activator stem has cleared the catches 259 and is nested in the gap 260 between the forks 258. Upon the activator stem clearing the catches 259, the forks 258 may return to an original resting configuration. Similar to the first embodiment, in other versions the forks 258 may not be deformable but rather a user applied force must merely overcome frictional resistance between the catches 259 and the stem of the activator mechanism 220.

So configured, the forks 258 at least partially surround the activator stem and reside at a location between the activator button 222 and the housing 206, and the forks 258 remain in contact with the activator button 222. When the activation prevention mechanism 250 is coupled to the device 200, a patient will not be able to intentionally or unintentionally depress the activator button 222 to actuate the device 200 because the motion of travel is obstructed by the forks 258.

To remove the activation prevention mechanism 250 from the device 200, a user may grasp the gripping portion 258 and pull the activation prevention mechanism 230 along the top surface 210 of the device 200 away from the activator button 222. As illustrated in FIGS. 15 and 16, the activation prevention mechanism 250 may include an indicator 262 (e.g., an arrow formed in the body 252) to assist in identifying the direction to pull the activation prevention mechanism 250. Upon pulling the activation prevention mechanism 250, the forks 258 may again slightly deform (or friction must be overcome) to allow the activator stem to clear the catches 259.

Figure 17:
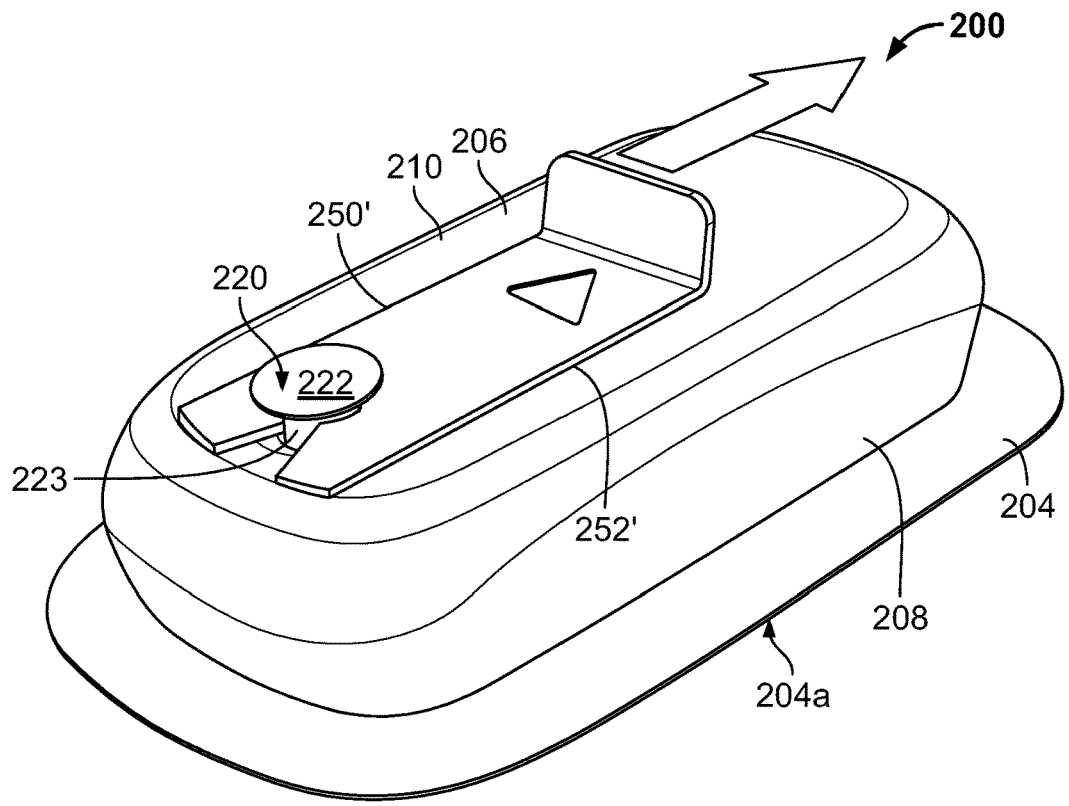
FIG. 17 is a perspective view of a seventh embodiment of an on-body injector with an activation prevention mechanism in accordance with the present disclosure.
Figure 18:
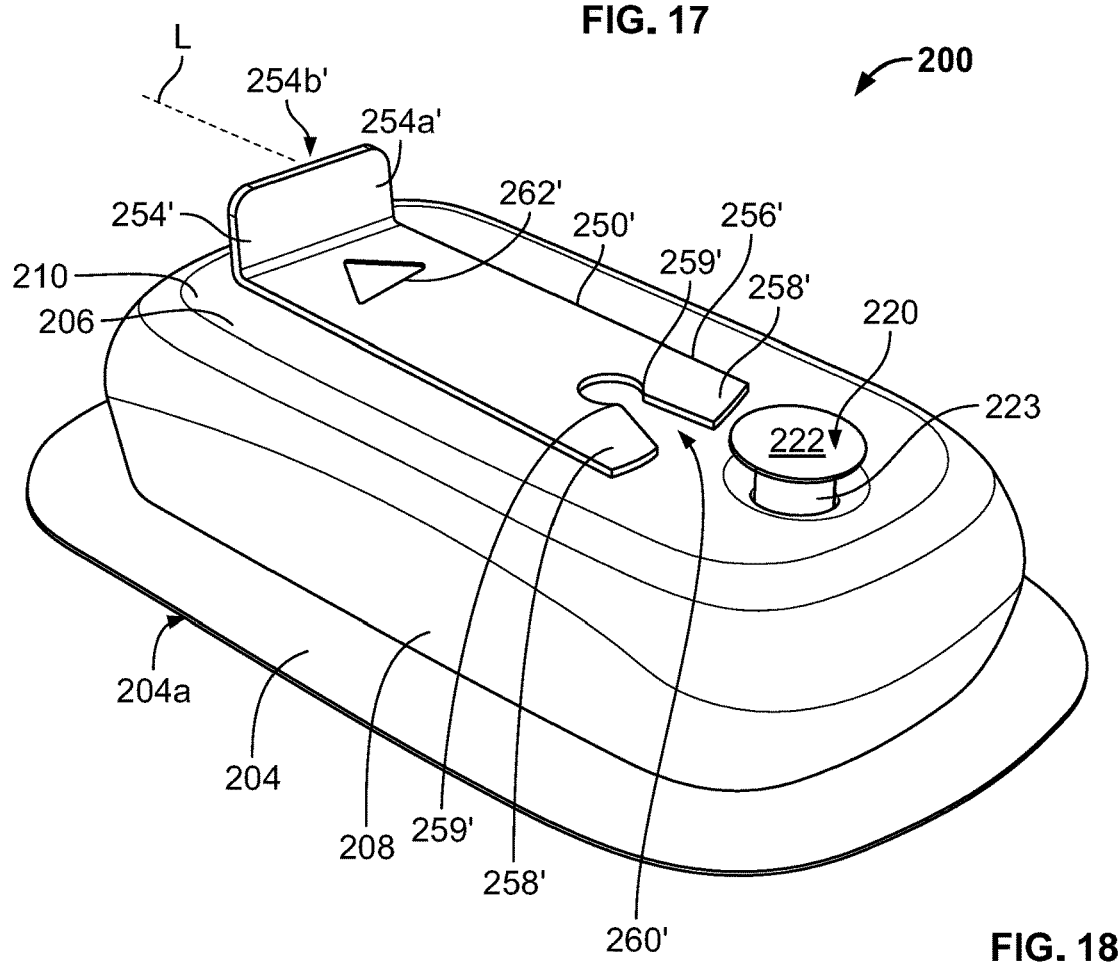
FIG. 18 is a perspective view of the on-body injector and activation prevention mechanism of FIG. 17 uncoupled from one another.
Figure 19:
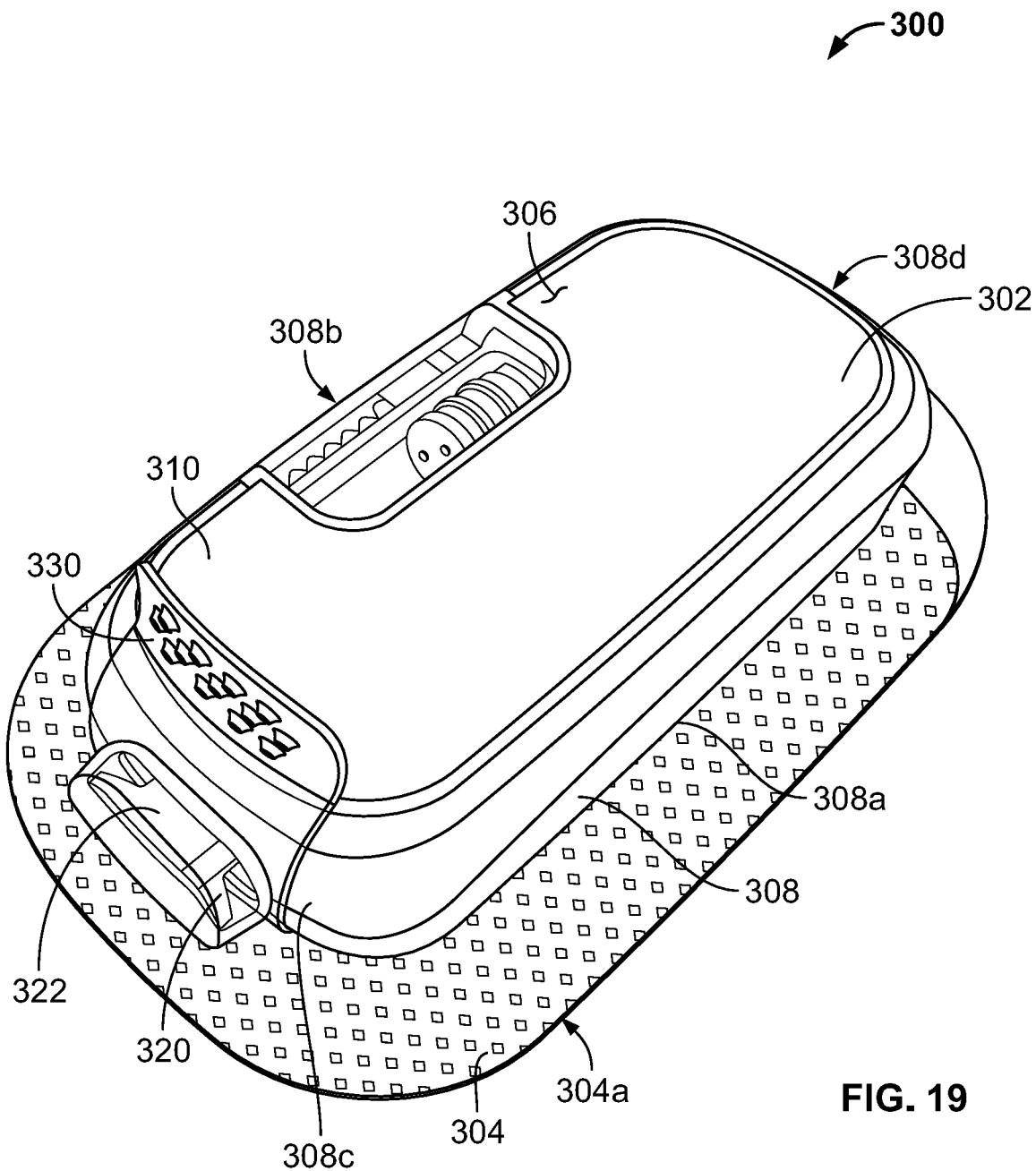
FIG. 19 is a perspective view of a eighth embodiment of an on-body injector with an activation prevention mechanism in accordance with the present disclosure.
Figure 20:
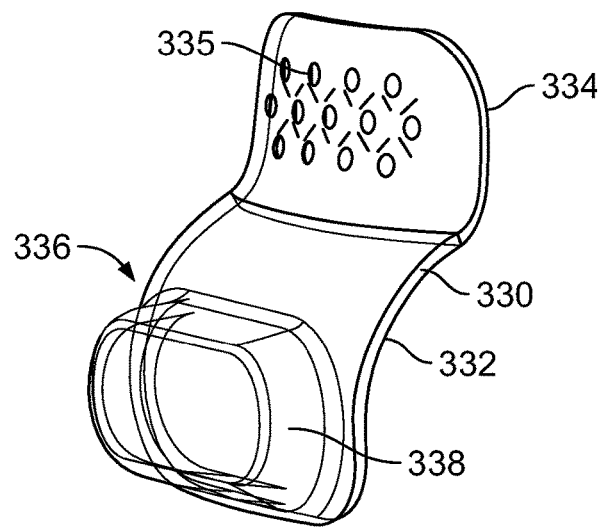
FIG. 20 is a perspective view of the activation prevention mechanism of FIG. 19.
Figure 21:
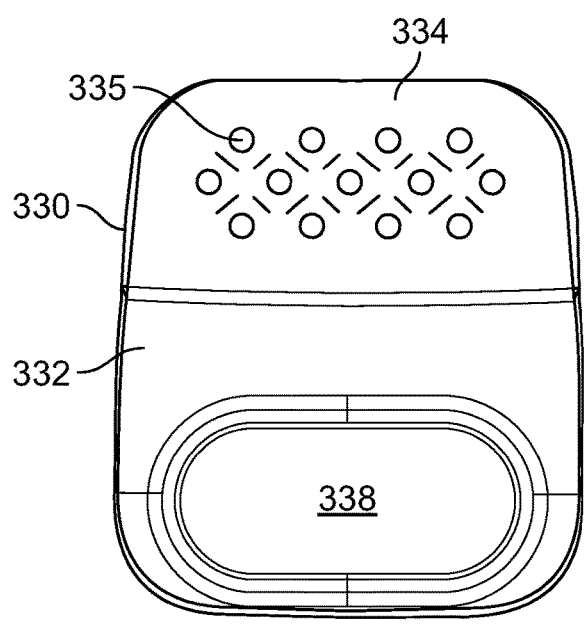
FIG. 21 is a front elevation view of the activation prevention mechanism of FIGS. 19 and 20.
Figure 22:
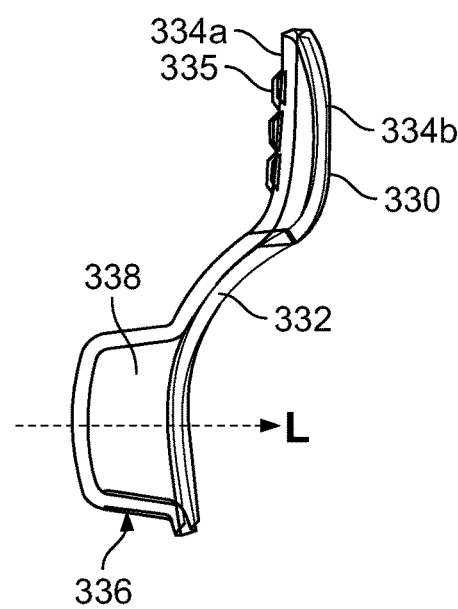
FIG. 22 is a right side elevation view of the activation prevention mechanism of FIGS. 19-21.

A seventh embodiment is shown in FIGS. 17 and 18 that includes an activation prevention mechanism 250' with a form similar to the mechanism 250 of FIGS. 15 and 16. As illustrated, the mechanism 250' includes a body 252' that is configured to extend along the top surface 210 of the device 200 when installed to prevent activation of the device 200. The body 252' includes a gripping portion 254', which in this form may have a planar configuration with opposing first and second surfaces 254a', 254b' that project away from a remaining portion of the body 252' at angle, such as between about 10 degrees to about 90 degrees, preferably between about 30 degrees to about 60 degrees, and more preferably about 45 degrees. So configured, the gripping portion 254' can be easily grasped by a user for selectively removing the activation prevention mechanism 250' from the housing 206 and for coupling the activation prevention mechanism 250' to the injector housing 206.

As shown in FIG. 18, the mechanism 250' further includes a coupling portion 256' that includes forks 258' with a gap or opening 260' defined therebetween. The gap 260' of this form has a keyhole shape with catches 259' and outwardly angled sides extending to the opening to the gap 260'. The relatively wider width at the opening of the gap 260' provides an easy location for a user to install the mechanism 250' on the device 200. The forks 258' may be of any shape and/or dimension that generally corresponds to a cross sectional shape and dimension of the activator stem. In the illustrated form, the forks 258' are generally symmetrical about axis L and include catches 259' that protrude inwardly towards axis L. These catches 259' engage the activator stem in order to increase the force required to remove the activation prevention mechanism 250' from the device 200. The coupling portion 236' (as well as the entirety of the activation prevention mechanism 230) may be constructed from a resilient material capable of slightly deforming when a force is applied thereto.

The body 252' can further includes an indicator 262' that may be a through opening as shown, a recess, or a projection providing tactile edges or surfaces. With this configuration, a user can slide the mechanism 250' across the device top surface 210 and press the gripping portion 254' in a direction generally parallel to the top surface 210 and the forks 258' may slightly deform outwardly (i.e., in a direction away from axis L) until the activator stem has cleared the catches 259' and is nested in the gap 260' between the forks 258'. Upon the activator stem clearing the catches 259', the forks 258' may return to an original resting configuration. Similar to the first embodiment, in other versions the forks 258' may not be deformable but rather a user applied force must merely overcome frictional resistance between the catches 259' and the stem of the activator mechanism 220. So configured, the forks 258' at least partially surround the activator stem and reside at a location between the activator button 222 and the housing 206 so that a patient will not be able to intentionally or unintentionally depress the activator button 222 to actuate the device 200 because the motion of travel is obstructed by the forks 258'. The mechanism 250' of this form can be installed and removed similarly to the above mechanism 150.

FIGS. 19-22 depict an eighth embodiment of an activation prevention mechanism 330 for an on-body drug delivery device 300. It is understood that the device 300 includes similar features and components as the devices 100 and 200 described with reference to FIGS. 1-18, thus reference numerals having identical two-digit suffixes (e.g., injector 302, adhesive applicator 304, and the like) have similar construction and operation as corresponding components in the devices 100, 200. Accordingly, these features and components will not be discussed in substantial detail. It is understood that features described with regard to the devices 100, 200, and/or 300 can be used interchangeably in any of these embodiments.

In this embodiment, the device 300 includes an activator mechanism 320 and an activation prevention mechanism 330. The activator mechanism 320 includes an activator button 322 and an activator stem (not shown) coupled to the activator button 322. The activator stem is disposed through an opening (not shown) of the sidewall 308c and is operably coupled to the drive mechanism. In some examples, a portion of the activator stem may extend outwardly beyond the sidewall 308c, and in other examples, the activator button 322 may be mounted flush with the sidewall 308c via a recess or other opening in order to allow the activator button 322 to be depressed inwardly toward the housing 306 in order to administer the drug.

The activation prevention mechanism 330 is operably coupled to the housing 306 to prevent the activator mechanism 320 from being inadvertently actuated. The activation prevention mechanism 330 includes a body 332 that connects a gripping portion 334 to a shell portion 336. The gripping portion 334 is used to selectively remove the activation prevention mechanism 330 from the housing 306 and for coupling the activation prevention mechanism 330 to the injector housing 306. The gripping portion 334 may include a first surface 334a and a second surface 334b, which may include any number of gripping features 335 (e.g., texturing, surface treatment, etching, dimpling, etc.). The body 332 may be curved, shaped and/or contoured to correspond to the shape of the sidewall 308. When the activation prevention mechanism 330 is coupled to the housing 306, the gripping portion 334 protrudes outwardly from the housing 306 to allow a user to grasp the gripping surfaces 334a, 334b in order to remove the activation prevention mechanism 330 from the device 300.

The shell portion 336 includes a protrusion 338 which may be of any shape and/or dimension that generally corresponds to a shape and/or dimension of the activator button 322. In some examples, the protrusion 338 is slightly larger than the activator button 322; in other examples, the protrusion 338 is dimensioned to be substantially larger than the activator button 322. The shell portion 336 (as well as the entirety of the activation prevention mechanism 330) may be constructed from a rigid material capable of withstanding a force exerted in the direction indicated by line L, which represents the direction in which the activator button 322 is depressed to cause the drive mechanism to administer the drug. In some examples, the shell portion 336 has a rigidity that is greater than a force required to depress the activator button 322. In some examples, the rigidity of the shell portion 336 is greater than a rigidity of the remainder of the activation prevention mechanism 330.

So configured, the protrusion 338 at least partially surrounds the activator button 322. In some examples, the protrusion 338 is dimensioned so that it frictionally engages the activator button 322 and thus remains affixed to the device. In other examples, the protrusion 338 is substantially larger than the activator button 322, thus an alternative and/or additional securing device is needed. In either example, an adhesive may be applied to the body 332 to releasably secure the activation prevention mechanism 330 to the housing 306. Upon applying the adhesive, the curved portion of the body 332 may be pressed against the sidewall 308c, thereby securing the activation prevention mechanism 330 to the device 300. When the activation prevention mechanism 330 is coupled to the device 300, a patient will not be able to intentionally or unintentionally depress the activator button 322 to actuate the device because the activator button 322 is encapsulated by the protrusion 338.

In some versions, the shell portion 336 can be constructed of a material that is clear, transparent, translucent, or opaque depending on the demands of the particular application and overall design of the injector.

To remove the activation prevention mechanism 330 from the device 300, a user may grasp the gripping portion 334 and pull the activation prevention mechanism 330 away from the device 300.

Figure 23:
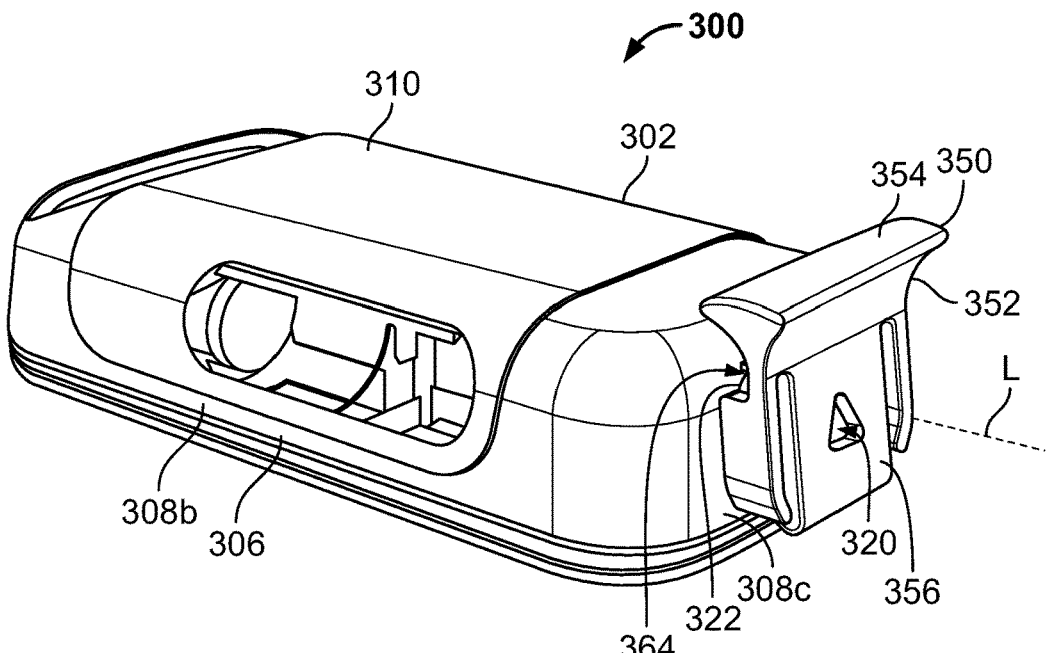
FIG. 23 is a perspective view of a ninth embodiment of an on-body injector with an activation prevention mechanism in accordance with the present disclosure.
Figure 24:
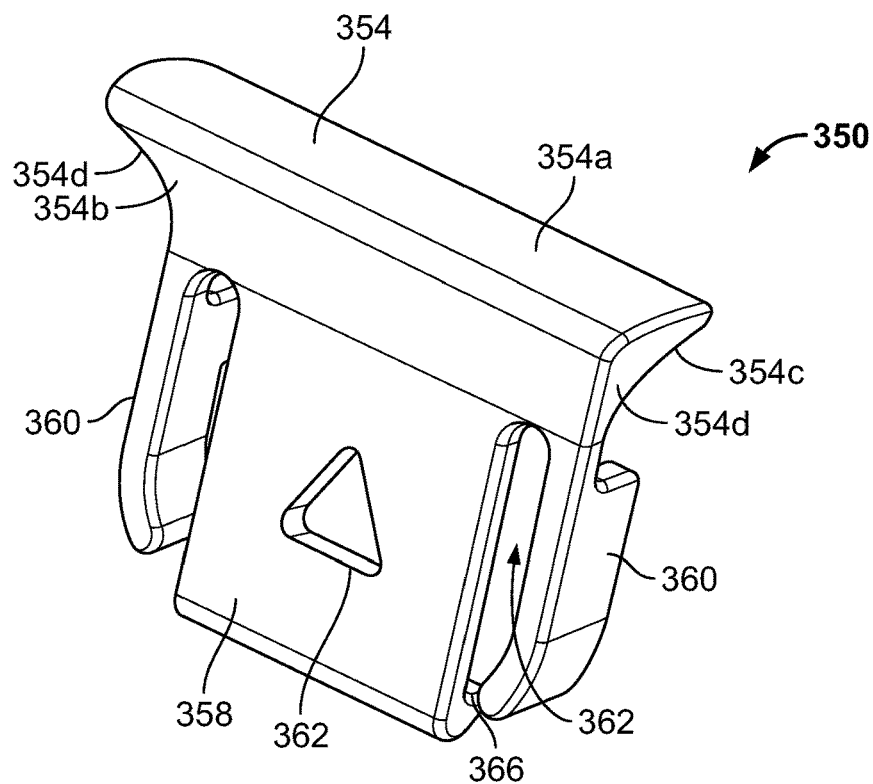
FIG. 24 is a perspective view of the activation prevention mechanism of FIG. 23.
Figure 25:
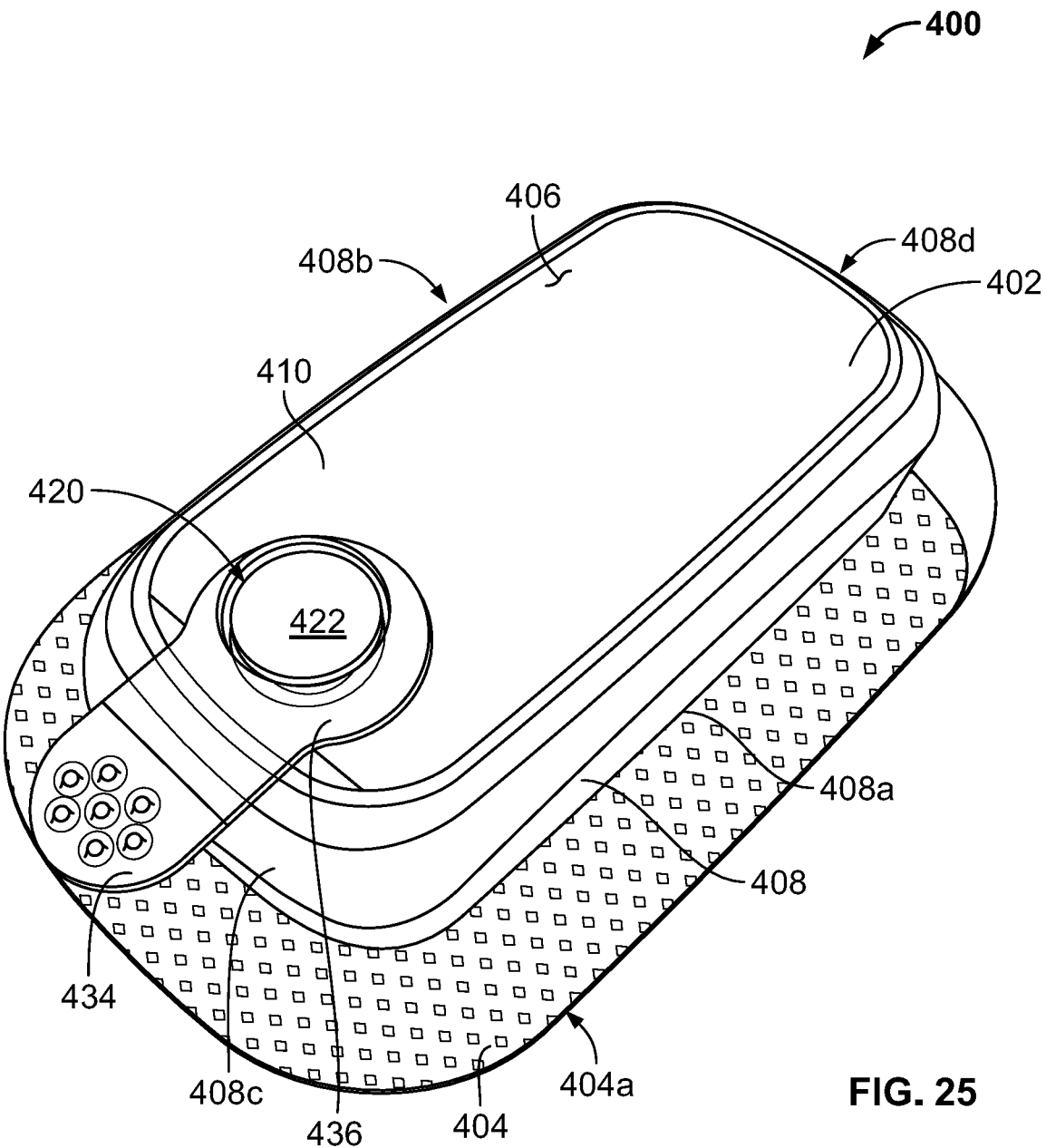
FIG. 25 is a perspective view of a tenth embodiment of an on-body injector with an activation prevention mechanism in accordance with the present disclosure.
Figure 26:
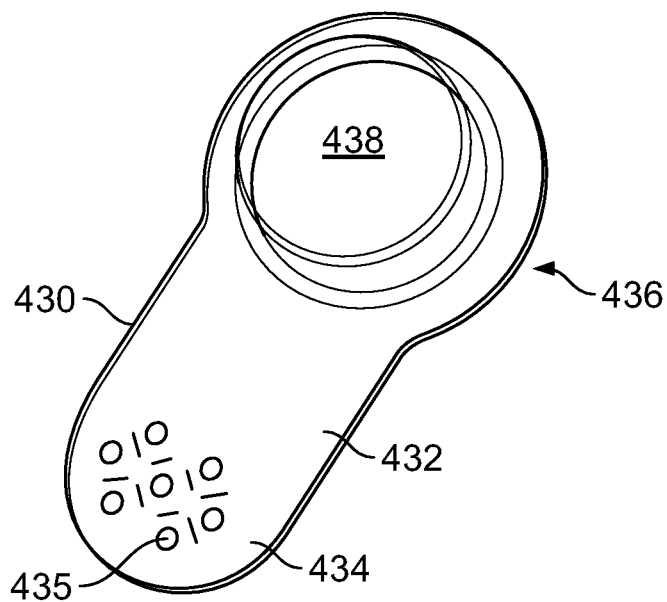
FIG. 26 is a perspective view of the activation prevention mechanism of FIG. 25.
Figure 27:
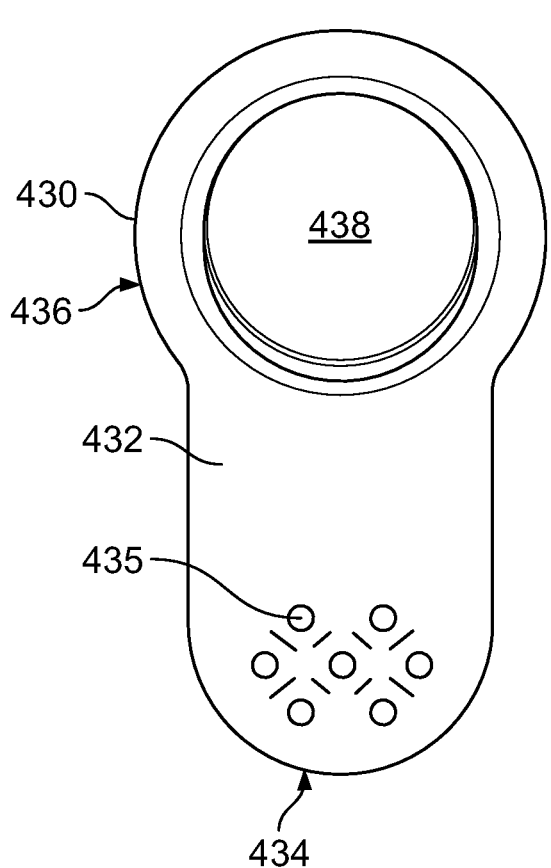
FIG. 27 is a top plan view of the activation prevention mechanism of FIGS. 25 and 26.
Figure 28:
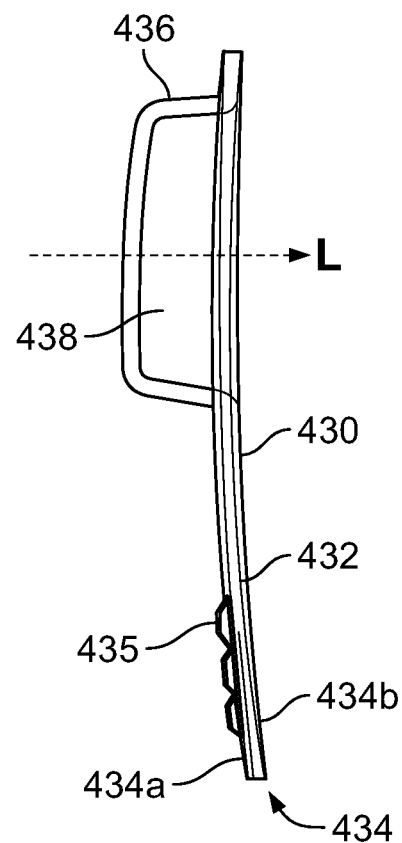
FIG. 28 is a right side elevation view of the activation prevention mechanism of FIGS. 25-27.

A ninth embodiment of an activation prevention mechanism 350 is shown in FIGS. 23 and 24. The activation prevention mechanism 350 of this embodiment is operably coupled to the housing 306 and/or the activator mechanism 320 to prevent the activator mechanism 320 from being inadvertently actuated (e.g., depressed). The activation prevention mechanism 350 includes a body 352 with a gripping portion 354 and a frame portion 356. The gripping portion 354 is used to selectively remove the activation prevention mechanism 350 from the housing 306 and for coupling the activation prevention mechanism 350 to the injector housing 306. The gripping portion 354 may include a top first surface 354a, a front second surface 354b, and a rear third surface 354c. In the illustrated example, the first surface 354a is a generally flat surface, and the second and third surfaces 354b, 354c are both curved surfaces, such that the gripping portion 354 has a generally T-shaped configuration. Further, the third surface 354c may be curved and/or shaped to correspond to the shape of the sidewall 308. If desired, the gripping portion 354 can also include side surfaces 354d that curve outwardly traveling from the frame portion 356 up to the first surface 354a. So configured, a user can grasp the gripping portion 354 between the second and third surfaces 354b, 354c and/or the side surfaces 354d. When the activation prevention mechanism 350 is coupled to the housing 306, the gripping portion 354 protrudes outwardly from the top surface 310 to allow a user to grasp the gripping portion 354 in order to remove the activation prevention mechanism 350 from the device 300.

The frame portion 356 includes a front wall 358 and lateral side prongs 360 that define a chamber 362 therebetween which may be of any shape and/or dimension that generally corresponds to a shape and/or dimension of the activator button 322. Preferably, the side prongs 360 have a depth larger than the activator button 322 so that the prongs 360 abut the device housing 306 preventing the button 322 from being actuated. In some examples, the frame portion 356 can further include a top wall 364 and a bottom wall or catch 366 that project above and below the activator button 322, respectively, with the mechanism 350 mounted to the device 300. So configured, the frame portion 356 is configured to enclose the button 322. Additionally, the button 322 can include a flange and the frame portion 356 can include inwardly projecting protrusions or lips configured to snap-fit the mechanism 350 to the button 322. For example, the top and bottom walls 356, 364 can both include protrusions so that the mechanism 350 is coupled to the button 322 on opposite sides thereof. Additionally, or alternatively, the side prongs 360 can include similarly configured protrusions. In other examples, the frame portion 356 is dimensioned so that it frictionally engages the activator button 322 and thus remains affixed to the device.

The frame portion 356 (as well as the entirety of the activation prevention mechanism 350) may be constructed from a rigid material capable of withstanding forces exerted in the direction indicated by line L, which represents the direction in which the activator button 322 is depressed to cause the drive mechanism to administer the drug. In some examples, the frame portion 356 has a rigidity that is greater than a force required to depress the activator button 322. In some examples, the rigidity of the frame portion 356 is greater than a rigidity of the remainder of the activation prevention mechanism 350.

So configured, the frame portion 356 at least partially surrounds the activator button 322. When the activation prevention mechanism 350 is coupled to the device 300, a patient will not be able to intentionally or unintentionally depress the activator button 322 to actuate the device because the activator button 322 is encapsulated by the frame portion 356. To remove the activation prevention mechanism 330 from the device 300, a user may grasp the gripping portion 354 and pull the activation prevention mechanism 350 away from the device 300, such as by pulling the gripping portion 354 forwardly.

FIGS. 25-28 depict a tenth embodiment of an activator mechanism 420 for an on-body drug delivery device 400. It is understood that the device 400 includes similar features and components as the devices 100, 200, and 300 described with reference to FIGS. 1-24, thus reference numerals having identical two-digit suffixes (e.g., injector 402, adhesive applicator 404, and the like) have similar construction and operation as corresponding components in the devices 100, 200, 300. Accordingly, these features and components will not be discussed in substantial detail. It is understood that features described with regard to the devices 100, 200, 300, and/or 400 can be used interchangeably in any of these embodiments.

Like the device 200 of FIGS. 9-18, the device 400 includes an activator mechanism 420 having an activator button 422 and an activator stem (not shown) coupled to the activator button 422. The activator stem is disposed through an opening (not shown) of the top surface 410 and is operably coupled to the drive mechanism. Similar to the device 300 of FIGS. 19-24, a portion of the activator stem may extend outwardly beyond the top surface 410, and in other examples, the activator button 422 may be mounted flush with the top surface 410 via a recess or other opening in order to allow the activator button 422 to be depressed inwardly toward the housing 406 in order to administer the drug.

The activation prevention mechanism 430 is operably coupled to the housing 406 to prevent the activator mechanism 420 from being inadvertently activated. The activation prevention mechanism 430 includes a body 432 that connects a gripping portion 434 to a shell portion 436. The gripping portion 434 is used to selectively remove the activation prevention mechanism 430 from the housing 406 and for coupling the activation prevention mechanism 430 to the injector housing 406. The gripping portion 434 may include a first surface 434a and a second surface 434b, which may include any number of gripping features 435. The body 432 may be curved and/or shaped to correspond to the shape of the top surface 410 and/or the sidewall 408. When the activation prevention mechanism 430 is coupled to the housing 406, the gripping portion 434 protrudes outwardly from the housing 406 to allow a user to grasp the gripping surfaces 434a, 434b in order to remove the activation prevention mechanism 430 from the device 400.

The shell portion 436 includes a protrusion 438 which may be of any shape and/or dimension that generally corresponds to a shape and/or dimension of the activator button 422. In some examples, the protrusion 438 is slightly larger than the activator button 422; in other examples, the protrusion 438 is dimensioned to be substantially larger than the activator button 422. The shell portion 436 (as well as the entirety of the activation prevention mechanism 430) may be constructed from a rigid material capable of withstanding a force exerted in the direction indicated by line L, which represents the direction in which the activator button 422 is depressed to cause the drive mechanism to administer the drug. In some examples, the shell portion 436 has a rigidity that is greater than a force required to depress the activator button 422, and may include a rigidity that is greater than a rigidity of the remainder of the activation prevention mechanism. In some versions, the shell portion 436 can be constructed of a material that is clear, transparent, translucent, or opaque depending on the demands of the particular application and overall design of the injector.

So configured, the protrusion 438 at least partially surrounds the activator button 422. In some examples, the protrusion 438 is dimensioned so that it frictionally engages the activator button 422 and thus remains affixed to the device. In other examples, the protrusion 438 is substantially larger than the activator button 422, thus an alternative and/or additional securing device is needed. In either example, an adhesive may be applied to the body 432 to releasably secure the activation prevention mechanism 430 to the housing 406. Upon applying the adhesive, the body 432 may be pressed against the sidewall 408c, thereby securing the activation prevention mechanism 430 to the device 400. When the activation prevention mechanism 430 is coupled to the device 400, a patient will not be able to intentionally or unintentionally depress the activator button 422 to actuate the device because the activator button 422 is encapsulated by the protrusion 438.

To remove the activation prevention mechanism 430 from the device 400, a user may grasp the gripping portion 434 and pull the activation prevention mechanism 430 away from the device 400.

While the embodiments described in FIGS. 19-28 show the respective shell portions as fully encapsulating or enclosing the activator mechanisms, it should be appreciated that in other versions the shell portions may less than fully encapsulate or enclose the activator mechanisms. That is, in some versions, the shell portion may simply provide one or more bars or ribs that reduce access to the activator mechanism but do not necessarily fully prevent access.

Figure 29:
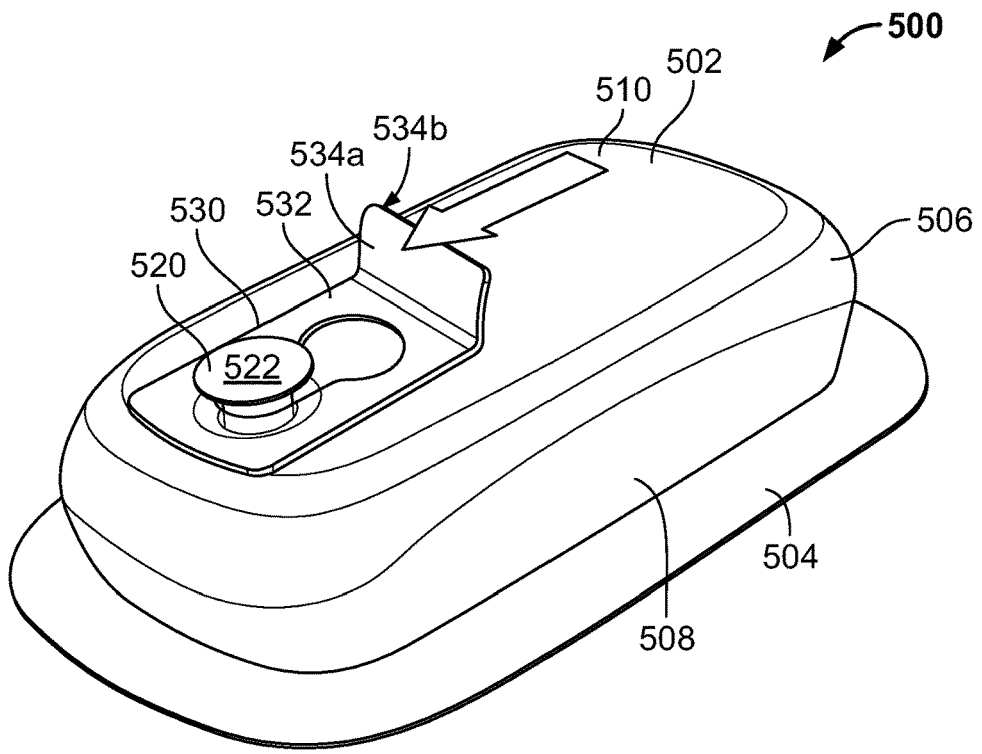
FIG. 29 is a perspective view of a eleventh embodiment of an on-body injector with an activation prevention mechanism in accordance with the present disclosure.
Figure 30:
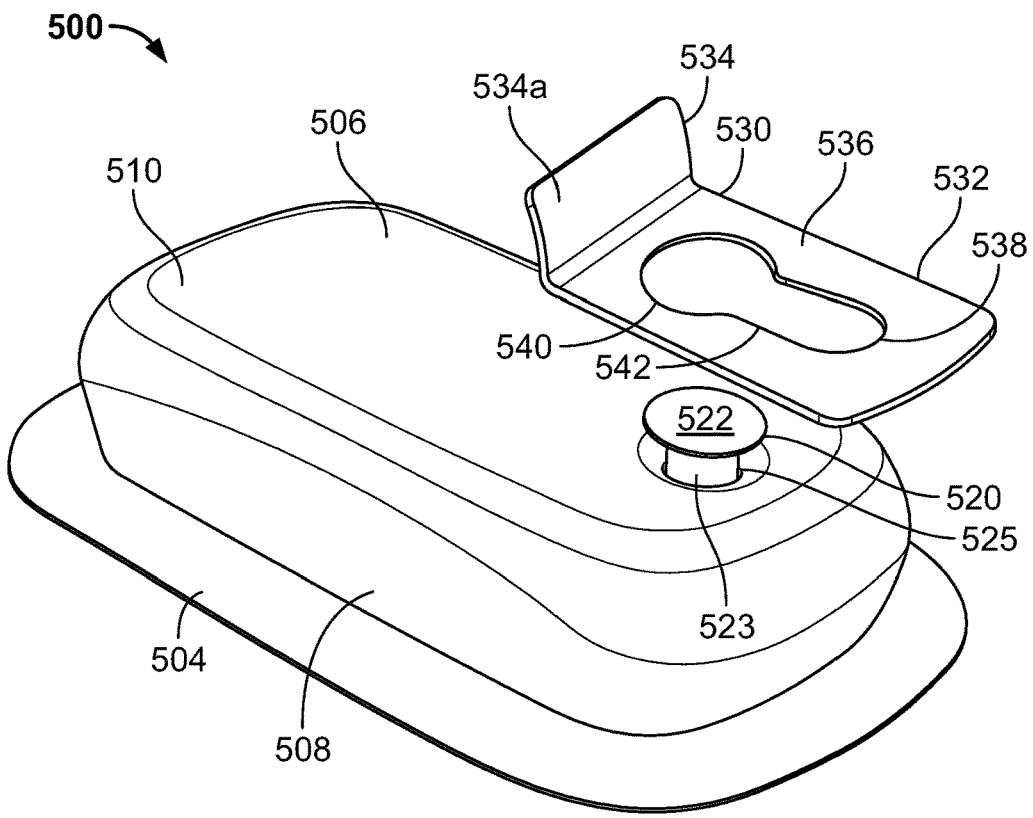
FIG. 30 is a perspective view of the on-body injector and activation prevention mechanism of FIG. 29 uncoupled from one another.

FIGS. 29 and 30 depict an eleventh embodiment of an activation prevention mechanism 530 for an on-body drug delivery device 500. It is understood that the device 500 includes similar features and components as the devices 100, 200, 300, 400 described with reference to FIGS. 1-28, thus reference numerals having identical two-digit suffixes (e.g., injector 502, adhesive applicator 504, and the like) have similar construction and operation as corresponding components in the devices 100, 200, 300, 400. Accordingly, these features and components will not be discussed in substantial detail. It is understood that features described with regard to the devices 100, 200, 300, 400, and/or 500 can be used interchangeably in any of these embodiments.

Like the device 200 of FIGS. 9-18, the device 500 includes an activator mechanism 520 having an activator button 522 and an activator stem 523 coupled to the activator button 522. The activator stem 523 is disposed through an opening 525 of the top surface 510 and is operably coupled to the drive mechanism. Similar to the device 300 of FIGS. 19-24, a portion of the activator stem 523 may extend outwardly beyond the top surface 510 in order to allow the activator button 522 to be depressed inwardly toward the housing 506 in order to administer the drug.

The activation prevention mechanism 530 is operably coupled to the housing 506 to prevent the activator mechanism 520 from being inadvertently activated. The activation prevention mechanism 530 includes a body 532 that is configured to extend along the top surface 510 of the device 500 when installed to prevent activation of the device 500. The body 532 includes a gripping portion 534 that projects away from the top surface 510 so that the gripping portion 534 can be easily grasped by a user for selectively removing the activation prevention mechanism 530 from the housing 506 and for coupling the activation prevention mechanism 530 to the injector housing 506. The gripping portion 534 projects away from the remaining portion of the body 532 and includes opposing first and second surfaces 534a, 534b. In the illustrated form, the gripping portion 534 has a curvature, which can be convex as shown or concave, as desired. Alternatively, the gripping portion 534 can have a generally planar configuration.

The activation prevention mechanism 530 further includes a coupling portion 536 that includes an opening 538 extending therethrough. The opening 538 includes an insertion portion 540 and a retention portion 542. The insertion portion 540 has dimensions larger than the activator button 522 so that the activator button 522 can pass therethrough and the retention portion 542 has a width smaller than the activator button 522, but larger than the activator stem 523. So configured, the activation prevention mechanism 530 can be coupled to the device 500 by inserting the button 522 through the insertion portion 540 and sliding the mechanism 530 along the top surface 510 of the device 500 so that the activator stem 523 slides into the retention portion 542. If desired, the retention portion 542 can be sized to frictionally engage the activator stem 523 in order to increase the force required to remove the activation prevention mechanism 530 from the device 500. When the activation prevention mechanism 530 is coupled to the device 500, a patient will not be able to intentionally or unintentionally depress the activator button 522 to actuate the device 500 because the motion of travel is obstructed by the coupling portion 536.

To remove the activation prevention mechanism 530 from the device 500, a user may grasp the gripping portion 534 and push the gripping portion 534 along the top surface 510 of the device 500 towards the activator button 522 to align the activator button 522 with the insertion portion 540. Thereafter, the user can lift the mechanism 530 off the device 500 or depress the activator button 522 through the insertion portion 540.

Figure 31:
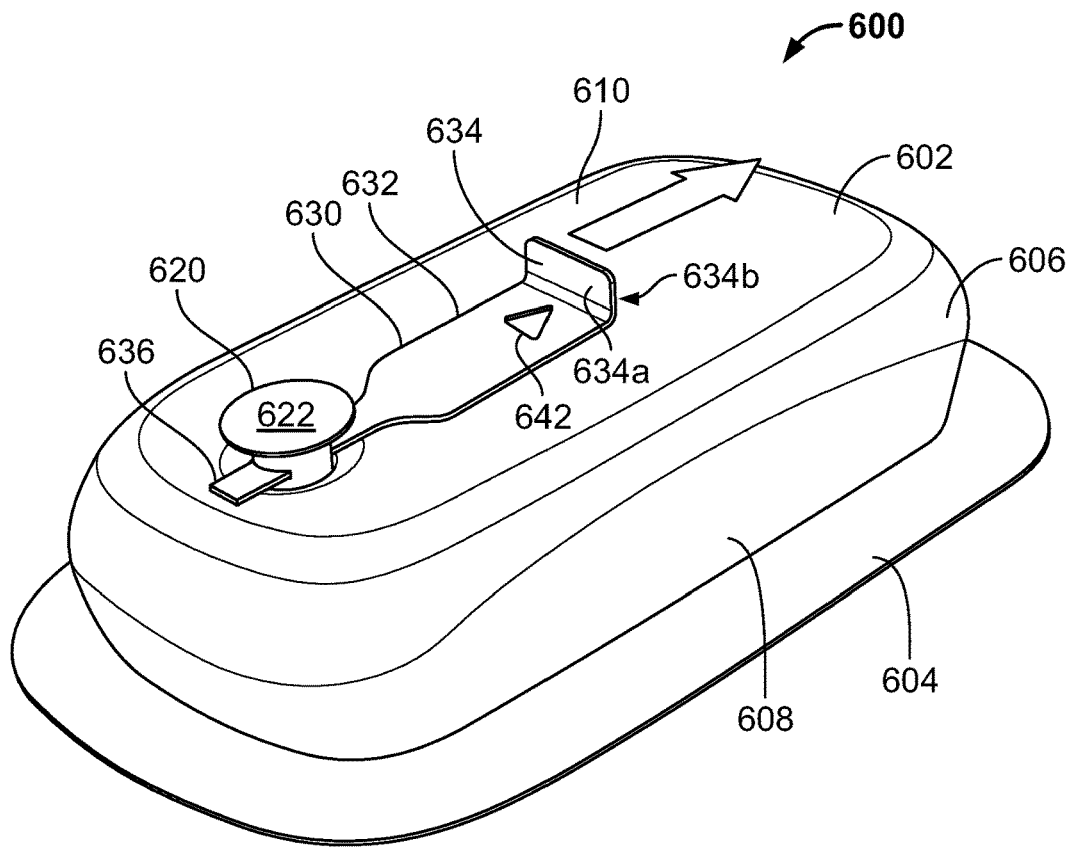
FIG. 31 is a perspective view of a twelfth embodiment of an on-body injector with an activation prevention mechanism in accordance with the present disclosure.
Figure 32:
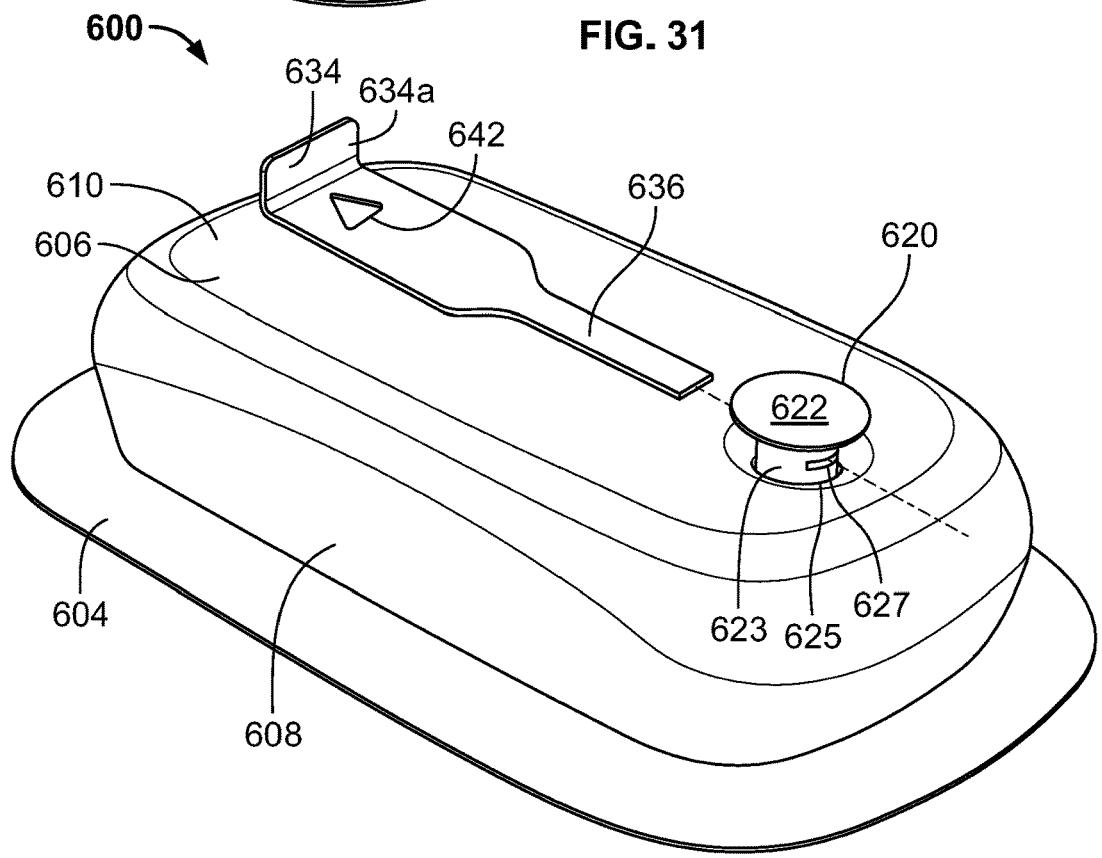
FIG. 32 is a perspective view of the on-body injector and activation prevention mechanism of FIG. 31 uncoupled from one another.

FIGS. 31 and 32 depict a twelfth embodiment of an activation prevention mechanism 630 for an on-body drug delivery device 600. It is understood that the device 600 includes similar features and components as the devices 100, 200, 300, 400, 500 described with reference to FIGS. 1-30, thus reference numerals having identical two-digit suffixes (e.g., injector 602, adhesive applicator 604, and the like) have similar construction and operation as corresponding components in the devices 100, 200, 300, 400, 500. Accordingly, these features and components will not be discussed in substantial detail. It is understood that features described with regard to the devices 100, 200, 300, 400, 500, and/or 600 can be used interchangeably in any of these embodiments Like the device 200 of FIGS. 9-18, the device 600 includes an activator mechanism 620 having an activator button 622 and an activator stem 623 coupled to the activator button 622. The activator stem is disposed through an opening 625 of the top surface 610 and is operably coupled to the drive mechanism. Similar to the device 300 of FIGS. 19-24, a portion of the activator stem may extend outwardly beyond the top surface 610 in order to allow the activator button 622 to be depressed inwardly toward the housing 606 in order to administer the drug.

The activation prevention mechanism 630 is operably coupled to the activator mechanism 620 to prevent the activator mechanism 620 from being inadvertently activated. The activation prevention mechanism 630 includes a body 632 that is configured to extend along the top surface 610 of the device 600 when installed to prevent activation of the device 600. The body 632 includes a gripping portion 634 that projects away from the top surface 610 so that the gripping portion 634 can be easily grasped by a user for selectively removing the activation prevention mechanism 630 from the housing 606 and for coupling the activation prevention mechanism 630 to the activator mechanism 620. The gripping portion 634 projects away from the remaining portion of the body 632 and includes opposing first and second surfaces 634a, 634b. In the illustrated form, the gripping portion 634 has a planar configuration projecting away from the top surface 610 at an angle with respect thereto. Alternatively, the gripping portion 634 can have a curvature, which can be convex or concave, as desired.

The activation prevention mechanism 630 further includes a coupling portion 636 that has an elongate configuration. The activator stem 623 includes an opening 627 that extends therethrough that is sized and configured to receive the coupling portion 636 of the activation prevention mechanism 630 therethrough. So configured, the activation prevention mechanism 630 can be coupled to the device 600 by inserting coupling portion 636 through the opening 627 in the activator stem 623. If desired, the coupling portion 636 and opening 627 can be sized so that the coupling portion 636 frictionally engages the sides of the opening 627 in order to increase the force required to remove the activation prevention mechanism 630 from the device 600.

When the activation prevention mechanism 630 is coupled to the device 600, a patient will not be able to intentionally or unintentionally depress the activator button 622 to actuate the device 600 because the motion of travel is obstructed by the coupling portion 636.

In the illustrated form, the coupling portion 636 has a flat configuration with a rectangular cross-section and the opening 627 has a corresponding shape. Of course, other shapes and sizes can also be utilized, such as circular, triangular, other polygons, curvilinear portions, and combinations thereof. In such cases, the opening 627 can have shapes corresponding or sized to receive the coupling portion 636 therethrough.

To remove the activation prevention mechanism 630 from the device 600, a user may grasp the gripping portion 634 and push the body 632 along the top surface 610 to remove the coupling portion 636 from the stem opening 627. Further, as illustrated in FIGS. 31 and 32, the activation prevention mechanism 630 may include an indicator 642 (e.g., an arrow formed in the body 632) to assist in identifying the direction to pull the activation prevention mechanism 630.

Figure 33:
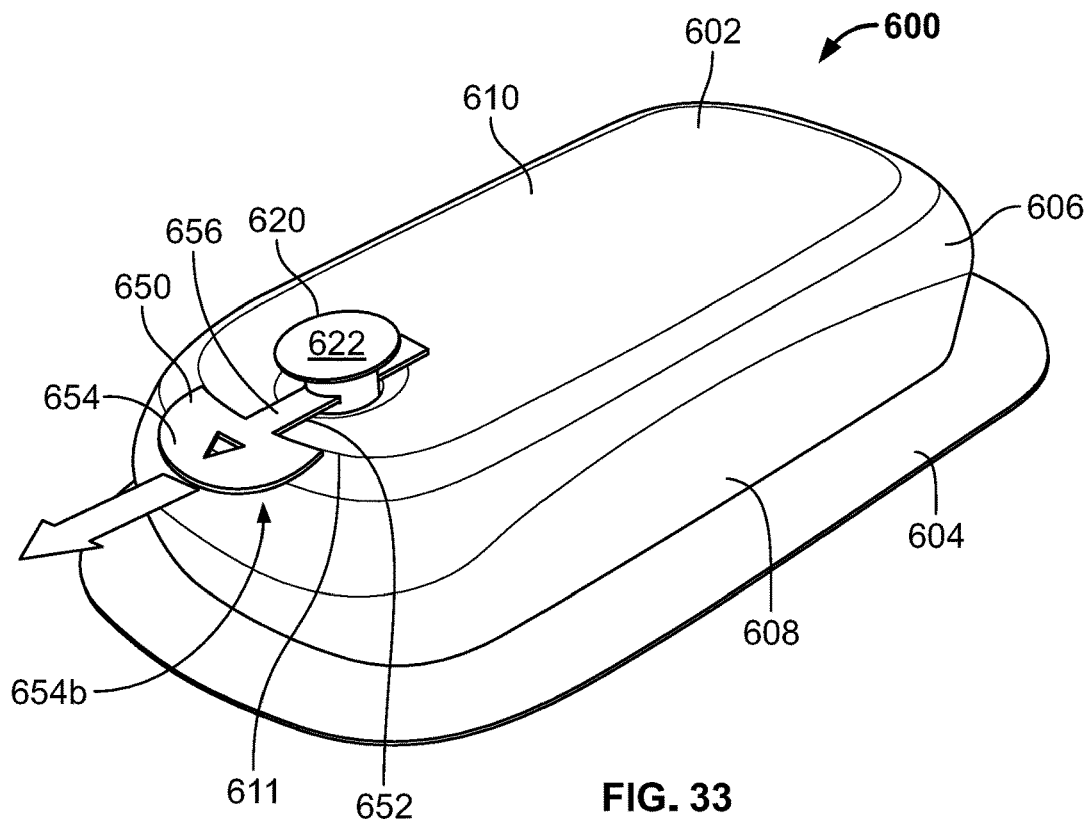
FIG. 33 is a perspective view of a thirteenth embodiment of an on-body injector with an activation prevention mechanism in accordance with the present disclosure.
Figure 34:
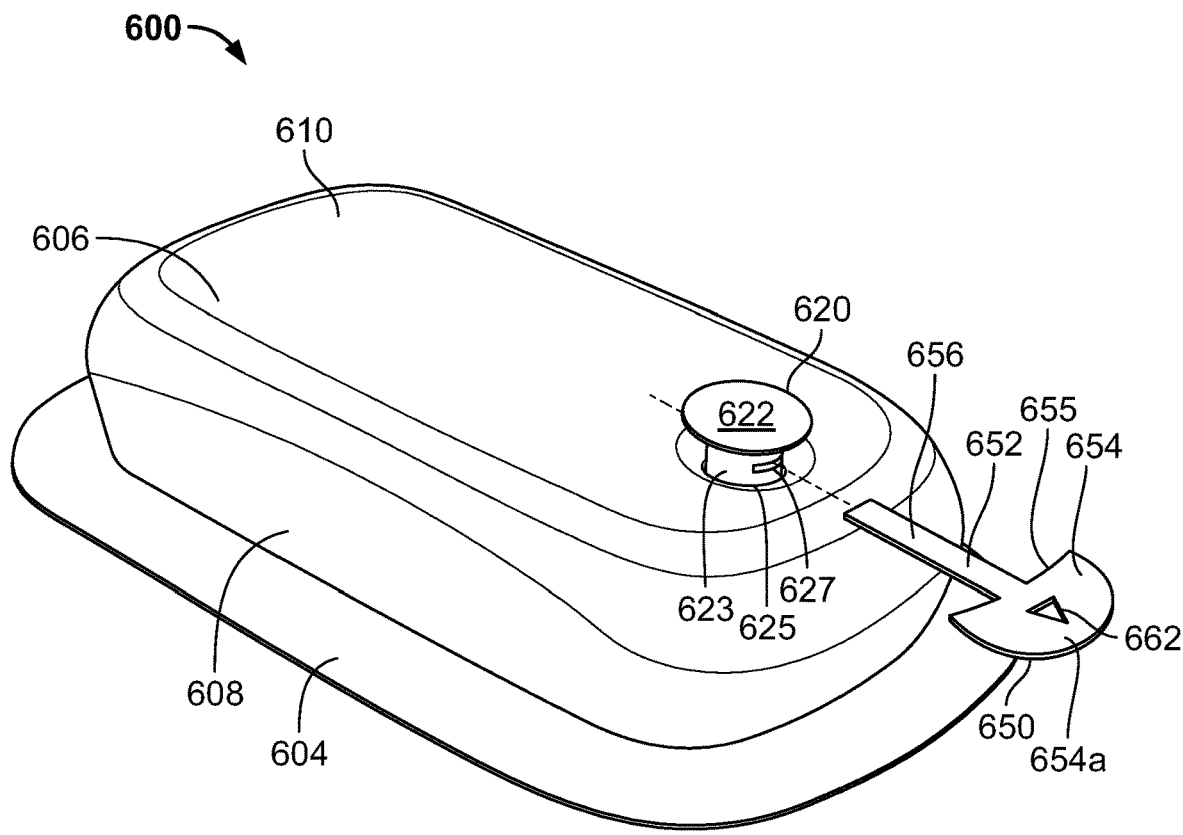
FIG. 34 is a perspective view of the on-body injector and activation prevention mechanism of FIG. 33 uncoupled from one another.

A thirteenth embodiment of an activation prevention mechanism 650 is shown in FIGS. 33 and 34 that operably couples to the activator mechanism 620 of the device 600 to prevent the activator mechanism 620 from being inadvertently actuated (e.g., depressed). The activation prevention mechanism 650 includes a body 652 with a gripping portion 654 and a coupling portion 656. The mechanism 650 of this form is similar to the above mechanism 630 except that the gripping portion 654 is configured to extend forwardly of the device 600 and the coupling portion 656 is configured to be inserted into the stem opening 627 from a position forwardly of the device 600. The gripping portion 654 of the illustrated form has a planar, tab configuration with opposing first and second surfaces 654a, 654b. The gripping portion 654 can include an edge 655 that is generally complementary to an edge 611 of the top surface 610. The gripping portion 654 can be easily grasped by a user for selectively removing the activation prevention mechanism 650 from the activator stem 623 and for coupling the activation prevention mechanism 650 to the activator stem 623.

Figure 35:
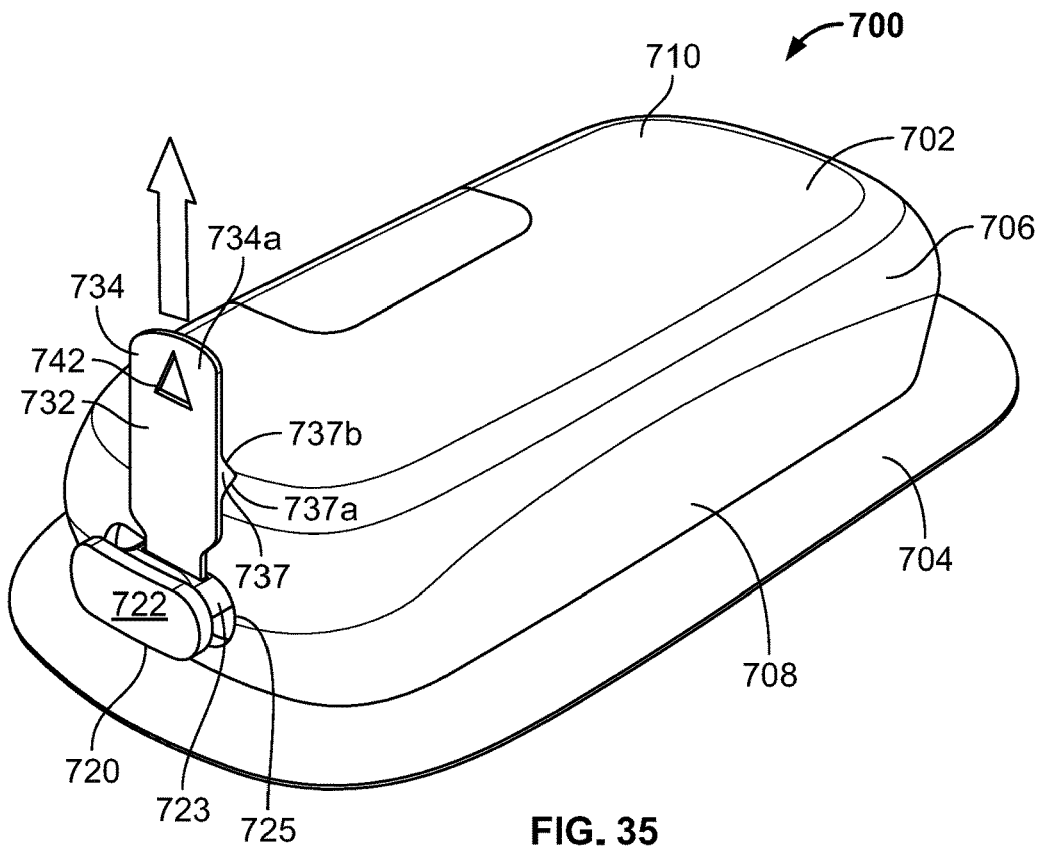
FIG. 35 is a perspective view of a fourteenth embodiment of an on-body injector with an activation prevention mechanism in accordance with the present disclosure.
Figure 36:
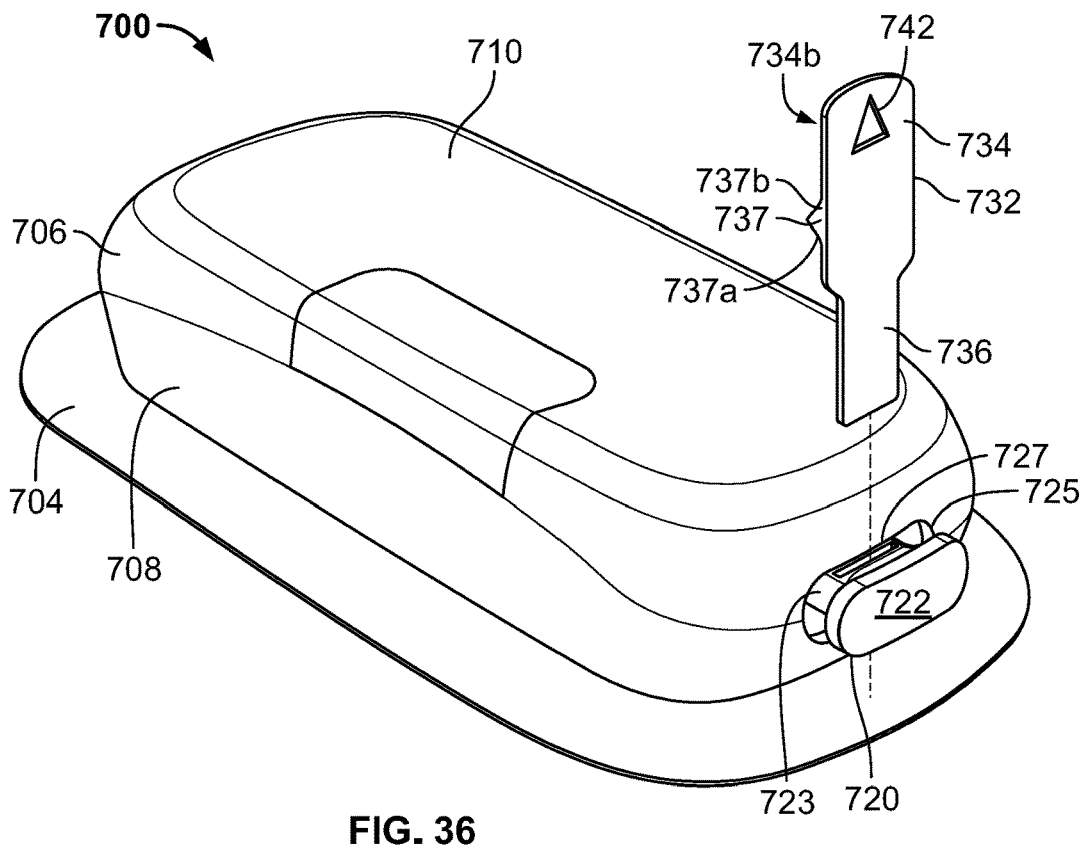
FIG. 36 is a perspective view of the on-body injector and activation prevention mechanism of FIG. 35 uncoupled from one another.

FIGS. 35 and 36 depict a fourteenth embodiment of an activation prevention mechanism 730 for an on-body drug delivery device 700. It is understood that the device 700 includes similar features and components as the devices 100, 200, 300, 400, 500, 600 described with reference to FIGS. 1-34, thus reference numerals having identical two-digit suffixes (e.g., injector 702, adhesive applicator 704, and the like) have similar construction and operation as corresponding components in the devices 100, 200, 300, 400, 500, 600. Accordingly, these features and components will not be discussed in substantial detail. It is understood that features described with regard to the devices 100, 200, 300, 400, 500, 600, and/or 700 can be used interchangeably in any of these embodiments.

In this embodiment, the device 700 includes an activator mechanism 720 with an activator button 722 and an activator stem 723 coupled to the activator button 722. The activator stem 723 is disposed through a front opening 725 of the housing 706 and is operably coupled to the drive mechanism. The activator stem 723 extends outwardly beyond a front portion of the housing 706.

The activation prevention mechanism 730 operably couples to the activator mechanism 720 of the device 700 to prevent the activator mechanism 720 from being inadvertently actuated (e.g., depressed). The activation prevention mechanism 730 includes a body 732 with a generally planar configuration. The body 732 includes an upper gripping portion 734 for selectively handling the activation prevention mechanism 730, e.g., for removing the mechanism 730 from the housing 706 and for coupling the mechanism 730 to the housing 706. The gripping portion 734 has a generally planar configuration with opposite first and second surfaces 734a, 734b. When the activation prevention mechanism 730 is coupled to the housing 706, the gripping portion 734 protrudes outwardly from the top surface 710 to allow a user to grasp the gripping surfaces 734a, 734b in order to remove the activation prevention mechanism 730 from the device 700. The gripping portion 734 can further include an indicator 742 (e.g., an arrow formed in the body 732) to assist in identifying the direction to pull the activation prevention mechanism 730. The indicator 742 may be a through opening as shown, a recess, or a projection providing tactile edges or surfaces for a user to get a better grip on the gripping portion 734.

As shown in FIGS. 35 and 36, the body 732 can include a rear projection 737 having a curved and/or shaped surface 737a that is configured to correspond to the shape of the sidewall 708 along the front thereof adjacent to the opening 725 so that the body 732 can nest along the housing 706 when the mechanism 730 is installed on the device 700. If desired, the rear projection 737 can have a peaked profile with a second curved and/or shaped surface 737b extending away from the sidewall 708 toward the gripping portion 734.

The activation prevention mechanism 730 further includes a coupling portion 736 that has an elongate or tab configuration. The activator stem 723 includes an opening 727 that extends therethrough that is sized and configured to receive the coupling portion 736 of the activation prevention mechanism 730 therethrough. So configured, the activation prevention mechanism 730 can be coupled to the device 700 by inserting coupling portion 736 through the opening 727 in the activator stem 723. If desired, the coupling portion 736 and opening 727 can be sized so that the coupling portion 736 frictionally engages the sides of the opening 727 in order to increase the force required to remove the activation prevention mechanism 730 from the device 700. When the activation prevention mechanism 730 is coupled to the device 700, a patient will not be able to intentionally or unintentionally depress the activator button 722 to actuate the device 700 because the motion of travel is obstructed by the coupling portion 736 abutting the activator stem 723 and device housing 706.

In the illustrated form, the coupling portion 736 has a flat configuration with a rectangular cross-section and the opening 727 has a corresponding shape. Of course, other shapes and sizes can also be utilized, such as circular, triangular, other polygons, curvilinear portions, and combinations thereof. In such cases, the opening 727 can have shapes corresponding or sized to receive the coupling portion 736 therethrough.

The device 700 may be provided to patients with the activation prevention mechanism 730 already coupled thereto. However, to couple the activation prevention mechanism 730 to the device, a user may align the coupling portion 736 with the opening 727 of the activator stem 723 and insert the coupling portion 736 therein. The coupling portion 736 can be sized to extend entirely therethrough. To remove the activation prevention mechanism 730 from the device 700, a user may grasp the gripping portion 734 and pull the body 732 upwardly away from the activator stem 723 until the coupling portion 736 clears the opening 727.

Figure 37:
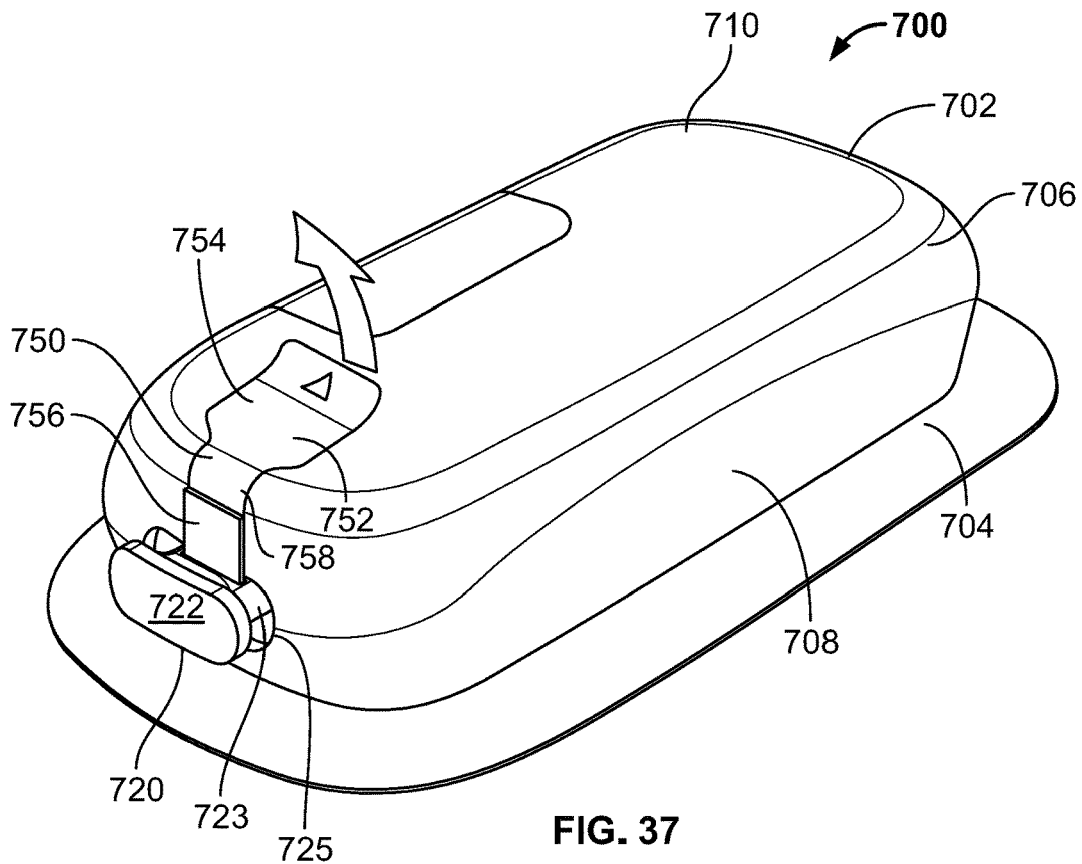
FIG. 37 is a perspective view of a fifteenth embodiment of an on-body injector with an activation prevention mechanism in accordance with the present disclosure.
Figure 38:
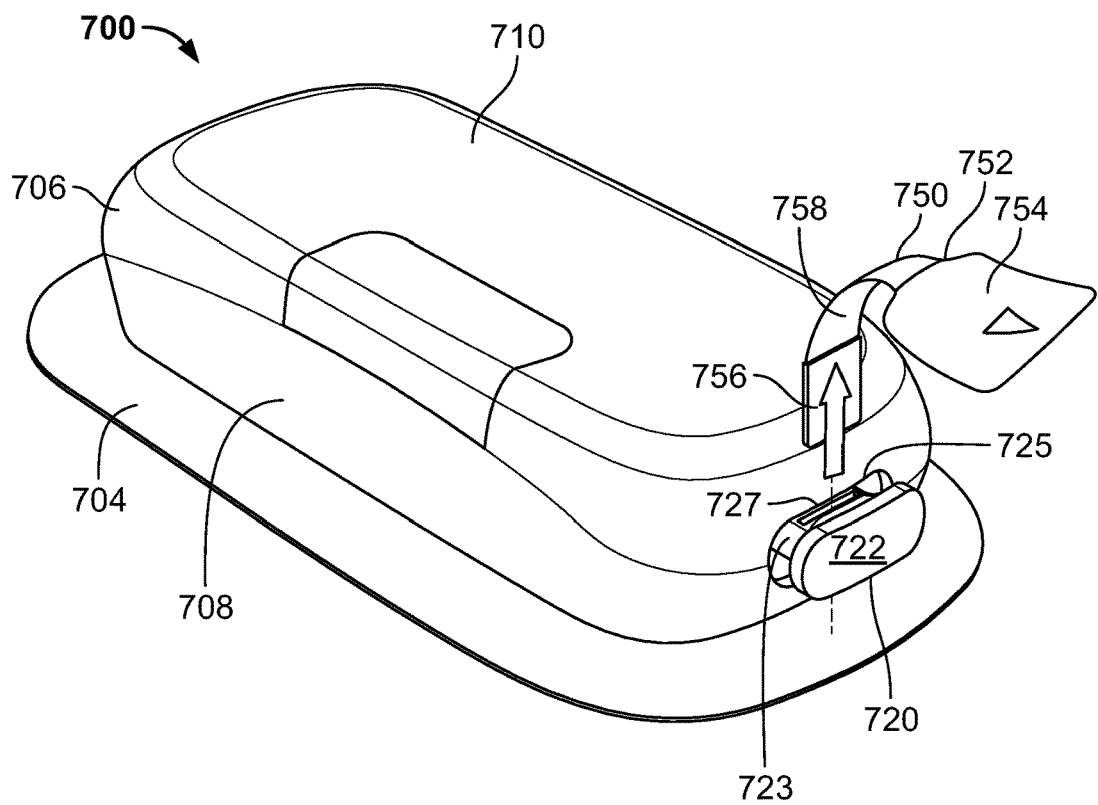
FIG. 38 is a perspective view of the on-body injector and activation prevention mechanism of FIG. 37 uncoupled from one another.

A fifteenth embodiment of an activation prevention mechanism 750 is shown in FIGS. 37 and 38 that operably couples to the activator mechanism 720 of the device 700 to prevent the activator mechanism 720 from being inadvertently actuated (e.g., depressed). The activation prevention mechanism 750 includes a body 752 with a gripping portion 754 and a coupling portion 756. The mechanism 750 of this form is similar to the above mechanism 730 except that the body 752 further includes a flexible intermediate portion 758 so that with the coupling portion 756 inserted into the stem opening 727, the flexible intermediate portion 758 can curve along the device housing 706 and the gripping portion 754 can extend along the device top surface 710. The gripping portion 754 can be substantially rigid or can be flexible similar to the intermediate portion 756. If desired, the gripping portion 754 can be adhered to the device top wall 710 to further secure the mechanism 750 to the device 700. The adhesive can be applied to the gripping portion 754, housing 706, or both. Moreover, the adhesive can be disposed to as to leave an adhesive-free gripping tab of the gripping portion 754 so that a user can easily grasp the gripping portion 754 to overcome the adhesive and remove the mechanism 750 from the device 700.

The device 700 may be provided to patients with the activation prevention mechanism 750 already coupled thereto. However, to couple the activation prevention mechanism 750 to the device, a user may align the coupling portion 756 with the opening 727 of the activator stem 723 and insert the coupling portion 756 therein. The coupling portion 756 can be sized to extend entirely therethrough. To remove the activation prevention mechanism 750 from the device 700, a user may grasp the gripping portion 754, pull the gripping portion 754 to overcome the adhesive, and pull the coupling portion 756 upwardly away from the activator stem 723 until the coupling portion 756 clears the opening 727.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

The above description describes various systems and methods for a drug delivery device having an activation prevention feature. It should be clear that the system, drug delivery device, or activation prevention features or methods can further comprise use of a drug product or medicament listed below with the caveat that the following list should neither be considered to be all inclusive nor limiting. The drug product or medicament will be contained in a reservoir. In some instances, the reservoir is a primary container that is either filled or pre-filled for treatment with the drug product or medicament. The primary container can be a cartridge or a pre-filled syringe.

For example, the drug delivery device or more specifically the reservoir of the device may be filled with colony stimulating factors, such as granulocyte colony-stimulating factor (G-CSF). Such G-CSF agents include, but are not limited to, Neupogen® (filgrastim) and Neulasta® (pegfilgrastim). In various other embodiments, the drug delivery device may be used with various pharmaceutical products, such as an erythropoiesis stimulating agent (ESA), which may be in a liquid or a lyophilized form. An ESA is any molecule that stimulates erythropoiesis, such as Epogen® (epoetin alfa), Aranesp® (darbepoetin alfa), Dynepo® (epoetin delta), Mircera® (methyoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin zeta, epoetin theta, and epoetin delta, as well as the molecules or variants or analogs thereof as disclosed in the following patents or patent applications, each of which is herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,986,047; 6,583,272; 7,084,245; and 7,271,689; and PCT Publication Nos. WO 91/05867; WO 95/05465; WO 96/40772; WO 00/24893; WO 01/81405; and WO 2007/136752.

An ESA can be an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, epoetin alfa, epoetin beta, epoetin delta, epoetin omega, epoetin iota, epoetin zeta, and analogs thereof, pegylated erythropoietin, carbamylated erythropoietin, mimetic peptides (including EMP1/hematide), and mimetic antibodies. Exemplary erythropoiesis stimulating proteins include erythropoietin, darbepoetin, erythropoietin agonist variants, and peptides or antibodies that bind and activate erythropoietin receptor (and include compounds reported in U.S. Publication Nos. 2003/0215444 and 2006/0040858, the disclosures of each of which is incorporated herein by reference in its entirety) as well as erythropoietin molecules or variants or analogs thereof as disclosed in the following patents or patent applications, which are each herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,830,851; 5,856,298; 5,986,047; 6,030,086; 6,310,078; 6,391,633; 6,583,272; 6,586,398; 6,900,292; 6,750,369; 7,030,226; 7,084,245; and 7,217,689; U.S. Publication Nos. 2002/0155998; 2003/0077753; 2003/0082749; 2003/0143202; 2004/0009902; 2004/0071694; 2004/0091961; 2004/0143857; 2004/0157293; 2004/0175379; 2004/0175824; 2004/0229318; 2004/0248815; 2004/0266690; 2005/0019914; 2005/0026834; 2005/0096461; 2005/0107297; 2005/0107591; 2005/0124045; 2005/0124564; 2005/0137329; 2005/0142642; 2005/0143292; 2005/0153879; 2005/0158822; 2005/0158832; 2005/0170457; 2005/0181359; 2005/0181482; 2005/0192211; 2005/0202538; 2005/0227289; 2005/0244409; 2006/0088906; and 2006/0111279; and PCT Publication Nos. WO 91/05867; WO 95/05465; WO 99/66054; WO 00/24893; WO 01/81405; WO 00/61637; WO 01/36489; WO 02/014356; WO 02/19963; WO 02/20034; WO 02/49673; WO 02/085940; WO 03/029291; WO 2003/055526; WO 2003/084477; WO 2003/094858; WO 2004/002417; WO 2004/002424; WO 2004/009627; WO 2004/024761; WO 2004/033651; WO 2004/035603; WO 2004/043382; WO 2004/101600; WO 2004/101606; WO 2004/101611; WO 2004/106373; WO 2004/018667; WO 2005/001025; WO 2005/001136; WO 2005/021579; WO 2005/025606; WO 2005/032460; WO 2005/051327; WO 2005/063808; WO 2005/063809; WO 2005/070451; WO 2005/081687; WO 2005/084711; WO 2005/103076; WO 2005/100403; WO 2005/092369; WO 2006/50959; WO 2006/02646; and WO 2006/29094.

Examples of other pharmaceutical products for use with the device may include, but are not limited to, antibodies such as Vectibix® (panitumumab), Xgeva™ (denosumab) and Prolia™ (denosamab); other biological agents such as Enbrel® (etanercept, TNF-receptor/Fc fusion protein, TNF blocker), Neulasta® (pegfilgrastim, pegylated filgrastim, pegylated G-CSF, pegylated hu-Met-G-CSF), Neupogen® (filgrastim, G-CSF, hu-MetG-CSF), and Nplate® (romiplostim); small molecule drugs such as Sensipar® (cinacalcet). The device may also be used with a therapeutic antibody, a polypeptide, a protein or other chemical, such as an iron, for example, ferumoxytol, iron dextrans, ferric glyconate, and iron sucrose. The pharmaceutical product may be in liquid form, or reconstituted from lyophilized form.

Among particular illustrative proteins are the specific proteins set forth below, including fusions, fragments, analogs, variants or derivatives thereof:

OPGL specific antibodies, peptibodies, and related proteins, and the like (also referred to as RANKL specific antibodies, peptibodies and the like), including fully humanized and human OPGL specific antibodies, particularly fully humanized monoclonal antibodies, including but not limited to the antibodies described in PCT Publication No. WO 03/002713, which is incorporated herein in its entirety as to OPGL specific antibodies and antibody related proteins, particularly those having the sequences set forth therein, particularly, but not limited to, those denoted therein: 9H7; 18B2; 2D8; 2E11; 16E1; and 22B3, including the OPGL specific antibodies having either the light chain of SEQ ID NO:2 as set forth therein in FIG. 2 and/or the heavy chain of SEQ ID NO:4, as set forth therein in FIG. 4, each of which is individually and specifically incorporated by reference herein in its entirety fully as disclosed in the foregoing publication;

Myostatin binding proteins, peptibodies, and related proteins, and the like, including myostatin specific peptibodies, particularly those described in U.S. Publication No. 2004/0181033 and PCT Publication No. WO 2004/058988, which are incorporated by reference herein in their entirety particularly in parts pertinent to myostatin specific peptibodies, including but not limited to peptibodies of the mTN8-19 family, including those of SEQ ID NOS:305-351, including TN8-19-1 through TN8-19-40, TN8-19 con1 and TN8-19 con2; peptibodies of the mL2 family of SEQ ID NOS:357-383; the mL15 family of SEQ ID NOS:384-409; the mL17 family of SEQ ID NOS:410-438; the mL20 family of SEQ ID NOS:439-446; the mL21 family of SEQ ID NOS:447-452; the mL24 family of SEQ ID NOS:453-454; and those of SEQ ID NOS:615-631, each of which is individually and specifically incorporated by reference herein in their entirety fully as disclosed in the foregoing publication;

IL-4 receptor specific antibodies, peptibodies, and related proteins, and the like, particularly those that inhibit activities mediated by binding of IL-4 and/or IL-13 to the receptor, including those described in PCT Publication No. WO 2005/047331 or PCT Application No. PCT/US2004/37242 and in U.S. Publication No. 2005/112694, which are incorporated herein by reference in their entirety particularly in parts pertinent to IL-4 receptor specific antibodies, particularly such antibodies as are described therein, particularly, and without limitation, those designated therein: L1H1; L1H2; L1H3; L1H4; L1H5; L1H6; L1H7; L1H8; L1H9; L1H10; L1H11; L2H1; L2H2; L2H3; L2H4; L2H5; L2H6; L2H7; L2H8; L2H9; L2H10; L2H11; L2H12; L2H13; L2H14; L3H1; L4H1; L5H1; L6H1, each of which is individually and specifically incorporated by reference herein in its entirety fully as disclosed in the foregoing publication;

Interleukin 1-receptor 1 ("IL1-R1") specific antibodies, peptibodies, and related proteins, and the like, including but not limited to those described in U.S. Publication No. 2004/097712, which is incorporated herein by reference in its entirety in parts pertinent to IL1-R1 specific binding proteins, monoclonal antibodies in particular, especially, without limitation, those designated therein: 15CA, 26F5, 27F2, 24E12, and 10H7, each of which is individually and specifically incorporated by reference herein in its entirety fully as disclosed in the aforementioned publication;

Ang2 specific antibodies, peptibodies, and related proteins, and the like, including but not limited to those described in PCT Publication No. WO 03/057134 and U.S. Publication No. 2003/0229023, each of which is incorporated herein by reference in its entirety particularly in parts pertinent to Ang2 specific antibodies and peptibodies and the like, especially those of sequences described therein and including but not limited to: L1(N); L1(N) WT; L1(N) 1K WT; 2×L1(N); 2×L1(N) WT; Con4 (N), Con4 (N) 1K WT, 2×Con4 (N) 1K; L1C; L1C 1K; 2×L1C; Con4C; Con4C 1K; 2×Con4C 1K; Con4-L1 (N); Con4-L1C; TN-12-9 (N); C17 (N); TN8-8(N); TN8-14 (N); Con 1 (N), also including anti-Ang 2 antibodies and formulations such as those described in PCT Publication No. WO 2003/030833 which is incorporated herein by reference in its entirety as to the same, particularly Ab526; Ab528; Ab531; Ab533; Ab535; Ab536; Ab537; Ab540; Ab543; Ab544; Ab545; Ab546; A551; Ab553; Ab555; Ab558; Ab559; Ab565; AbF1AbFD; AbFE; AbFJ; AbFK; AbG1D4; AbGC1E8; AbH1C12; AblA1; AblF; AblK, AblP; and AblP, in their various permutations as described therein, each of which is individually and specifically incorporated by reference herein in its entirety fully as disclosed in the foregoing publication;

NGF specific antibodies, peptibodies, and related proteins, and the like including, in particular, but not limited to those described in U.S. Publication No. 2005/0074821 and U.S. Pat. No. 6,919,426, which are incorporated herein by reference in their entirety particularly as to NGF-specific antibodies and related proteins in this regard, including in particular, but not limited to, the NGF-specific antibodies therein designated 4D4, 4G6, 6H9, 7H2, 14D10 and 14D11, each of which is individually and specifically incorporated by reference herein in its entirety fully as disclosed in the foregoing publication;

CD22 specific antibodies, peptibodies, and related proteins, and the like, such as those described in U.S. Pat. No. 5,789,554, which is incorporated herein by reference in its entirety as to CD22 specific antibodies and related proteins, particularly human CD22 specific antibodies, such as but not limited to humanized and fully human antibodies, including but not limited to humanized and fully human monoclonal antibodies, particularly including but not limited to human CD22 specific IgG antibodies, such as, for instance, a dimer of a human-mouse monoclonal hLL2 gamma-chain disulfide linked to a human-mouse monoclonal hLL2 kappa-chain, including, but limited to, for example, the human CD22 specific fully humanized antibody in Epratuzumab, CAS registry number 501423-23-0;

IGF-1 receptor specific antibodies, peptibodies, and related proteins, and the like, such as those described in PCT Publication No. WO 06/069202, which is incorporated herein by reference in its entirety as to IGF-1 receptor specific antibodies and related proteins, including but not limited to the IGF-1 specific antibodies therein designated L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, L52H52, and IGF-1R-binding fragments and derivatives thereof, each of which is individually and specifically incorporated by reference herein in its entirety fully as disclosed in the foregoing publication;

Also among non-limiting examples of anti-IGF-1R antibodies for use in the methods and compositions of the present invention are each and all of those described in:

(i) U.S. Publication No. 2006/0040358 (published Feb. 23, 2006), 2005/0008642 (published Jan. 13, 2005), 2004/0228859 (published Nov. 18, 2004), including but not limited to, for instance, antibody 1A (DSMZ Deposit No. DSM ACC 2586), antibody 8 (DSMZ Deposit No. DSM ACC 2589), antibody 23 (DSMZ Deposit No. DSM ACC 2588) and antibody 18 as described therein;

(ii) PCT Publication No. WO 06/138729 (published Dec. 28, 2006) and WO 05/016970 (published Feb. 24, 2005), and Lu et al. (2004), J. Biol. Chem. 279:2856-2865, including but not limited to antibodies 2F8, A12, and IMC-A12 as described therein;

(iii) PCT Publication No. WO 07/012614 (published Feb. 1, 2007), WO 07/000328 (published Jan. 4, 2007), WO 06/013472 (published Feb. 9, 2006), WO 05/058967 (published Jun. 30, 2005), and WO 03/059951 (published Jul. 24, 2003);

(iv) U.S. Publication No. 2005/0084906 (published Apr. 21, 2005), including but not limited to antibody 7C10, chimaeric antibody C7C10, antibody h7C10, antibody 7H2M, chimaeric antibody *7C10, antibody GM 607, humanized antibody 7C10 version 1, humanized antibody 7C10 version 2, humanized antibody 7C10 version 3, and antibody 7H2HM, as described therein;

(v) U.S. Publication Nos. 2005/0249728 (published Nov. 10, 2005), 2005/0186203 (published Aug. 25, 2005), 2004/0265307 (published Dec. 30, 2004), and 2003/0235582 (published Dec. 25, 2003) and Maloney et al. (2003), Cancer Res. 63:5073-5083, including but not limited to antibody EM164, resurfaced EM164, humanized EM164, huEM164 v1.0, huEM164 v1.1, huEM164 v1.2, and huEM164 v1.3 as described therein;

(vi) U.S. Pat. No. 7,037,498 (issued May 2, 2006), U.S. Publication Nos. 2005/0244408 (published Nov. 30, 2005) and 2004/0086503 (published May 6, 2004), and Cohen, et al. (2005), Clinical Cancer Res. 11:2063-2073, e.g., antibody CP-751,871, including but not limited to each of the antibodies produced by the hybridomas having the ATCC accession numbers PTA-2792, PTA-2788, PTA-2790, PTA-2791, PTA-2789, PTA-2793, and antibodies 2.12.1, 2.13.2, 2.14.3, 3.1.1, 4.9.2, and 4.17.3, as described therein;

(vii) U.S. Publication Nos. 2005/0136063 (published Jun. 23, 2005) and 2004/0018191 (published Jan. 29, 2004), including but not limited to antibody 19D12 and an antibody comprising a heavy chain encoded by a polynucleotide in plasmid 15H12/19D12 HCA (γ4), deposited at the ATCC under number PTA-5214, and a light chain encoded by a polynucleotide in plasmid 15H12/19D12 LCF (K), deposited at the ATCC under number PTA-5220, as described therein; and (viii) U.S. Publication No. 2004/0202655 (published Oct. 14, 2004), including but not limited to antibodies PINT-6A1, PINT-7A2, PINT-7A4, PINT-7A5, PINT-7A6, PINT-8A1, PINT-9A2, PINT-11A1, PINT-11A2, PINT-11A3, PINT-11A4, PINT-11A5, PINT-11A7, PINT-11A12, PINT-12A1, PINT-12A2, PINT-12A3, PINT-12A4, and PINT-12A5, as described therein; each and all of which are herein incorporated by reference in their entireties, particularly as to the aforementioned antibodies, peptibodies, and related proteins and the like that target IGF-1 receptors;

B-7 related protein 1 specific antibodies, peptibodies, related proteins and the like ("B7RP-1," also is referred to in the literature as B7H2, ICOSL, B7h, and CD275), particularly B7RP-specific fully human monoclonal IgG2 antibodies, particularly fully human IgG2 monoclonal antibody that binds an epitope in the first immunoglobulin-like domain of B7RP-1, especially those that inhibit the interaction of B7RP-1 with its natural receptor, ICOS, on activated T cells in particular, especially, in all of the foregoing regards, those disclosed in U.S. Publication No. 2008/0166352 and PCT Publication No. WO 07/011941, which are incorporated herein by reference in their entireties as to such antibodies and related proteins, including but not limited to antibodies designated therein as follow: 16H (having light chain variable and heavy chain variable sequences SEQ ID NO:1 and SEQ ID NO:7 respectively therein); 5D (having light chain variable and heavy chain variable sequences SEQ ID NO:2 and SEQ ID NO:9 respectively therein); 2H (having light chain variable and heavy chain variable sequences SEQ ID NO:3 and SEQ ID NO:10 respectively therein); 43H (having light chain variable and heavy chain variable sequences SEQ ID NO:6 and SEQ ID NO:14 respectively therein); 41H (having light chain variable and heavy chain variable sequences SEQ ID NO:5 and SEQ ID NO:13 respectively therein); and 15H (having light chain variable and heavy chain variable sequences SEQ ID NO:4 and SEQ ID NO:12 respectively therein), each of which is individually and specifically incorporated by reference herein in its entirety fully as disclosed in the foregoing publication;

IL-15 specific antibodies, peptibodies, and related proteins, and the like, such as, in particular, humanized monoclonal antibodies, particularly antibodies such as those disclosed in U.S. Publication Nos. 2003/0138421; 2003/023586; and 2004/0071702; and U.S. Pat. No. 7,153,507, each of which is incorporated herein by reference in its entirety as to IL-15 specific antibodies and related proteins, including peptibodies, including particularly, for instance, but not limited to, HuMax IL-15 antibodies and related proteins, such as, for instance, 14687;

IFN gamma specific antibodies, peptibodies, and related proteins and the like, especially human IFN gamma specific antibodies, particularly fully human anti-IFN gamma antibodies, such as, for instance, those described in U.S. Publication No. 2005/0004353, which is incorporated herein by reference in its entirety as to IFN gamma specific antibodies, particularly, for example, the antibodies therein designated 1118; 1118*; 1119; 1121; and 1121*. The entire sequences of the heavy and light chains of each of these antibodies, as well as the sequences of their heavy and light chain variable regions and complementarity determining regions, are each individually and specifically incorporated by reference herein in its entirety fully as disclosed in the foregoing publication and in Thakur et al. (1999), Mol. Immunol. 36:1107-1115. In addition, description of the properties of these antibodies provided in the foregoing publication is also incorporated by reference herein in its entirety. Specific antibodies include those having the heavy chain of SEQ ID NO:17 and the light chain of SEQ ID NO:18; those having the heavy chain variable region of SEQ ID NO:6 and the light chain variable region of SEQ ID NO:8; those having the heavy chain of SEQ ID NO:19 and the light chain of SEQ ID NO:20; those having the heavy chain variable region of SEQ ID NO:10 and the light chain variable region of SEQ ID NO:12; those having the heavy chain of SEQ ID NO:32 and the light chain of SEQ ID NO:20; those having the heavy chain variable region of SEQ ID NO:30 and the light chain variable region of SEQ ID NO:12; those having the heavy chain sequence of SEQ ID NO:21 and the light chain sequence of SEQ ID NO:22; those having the heavy chain variable region of SEQ ID NO:14 and the light chain variable region of SEQ ID NO:16; those having the heavy chain of SEQ ID NO:21 and the light chain of SEQ ID NO:33; and those having the heavy chain variable region of SEQ ID NO:14 and the light chain variable region of SEQ ID NO:31, as disclosed in the foregoing publication. A specific antibody contemplated is antibody 1119 as disclosed in the foregoing U.S. publication and having a complete heavy chain of SEQ ID NO:17 as disclosed therein and having a complete light chain of SEQ ID NO:18 as disclosed therein;

TALL-1 specific antibodies, peptibodies, and the related proteins, and the like, and other TALL specific binding proteins, such as those described in U.S. Publication Nos. 2003/0195156 and 2006/0135431, each of which is incorporated herein by reference in its entirety as to TALL-1 binding proteins, particularly the molecules of Tables 4 and 5B, each of which is individually and specifically incorporated by reference herein in its entirety fully as disclosed in the foregoing publications;

Parathyroid hormone ("PTH") specific antibodies, peptibodies, and related proteins, and the like, such as those described in U.S. Pat. No. 6,756,480, which is incorporated herein by reference in its entirety, particularly in parts pertinent to proteins that bind PTH;

Thrombopoietin receptor ("TPO-R") specific antibodies, peptibodies, and related proteins, and the like, such as those described in U.S. Pat. No. 6,835,809, which is herein incorporated by reference in its entirety, particularly in parts pertinent to proteins that bind TPO-R;

Hepatocyte growth factor ("HGF") specific antibodies, peptibodies, and related proteins, and the like, including those that target the HGF/SF:cMet axis (HGF/SF:c-Met), such as the fully human monoclonal antibodies that neutralize hepatocyte growth factor/scatter (HGF/SF) described in U.S. Publication No. 2005/0118643 and PCT Publication No. WO 2005/017107, huL2G7 described in U.S. Pat. No. 7,220,410 and OA-5d5 described in U.S. Pat. Nos. 5,686,292 and 6,468,529 and in PCT Publication No. WO 96/38557, each of which is incorporated herein by reference in its entirety, particularly in parts pertinent to proteins that bind HGF;

TRAIL-R2 specific antibodies, peptibodies, related proteins and the like, such as those described in U.S. Pat. No. 7,521,048, which is herein incorporated by reference in its entirety, particularly in parts pertinent to proteins that bind TRAIL-R2;

Activin A specific antibodies, peptibodies, related proteins, and the like, including but not limited to those described in U.S. Publication No. 2009/0234106, which is herein incorporated by reference in its entirety, particularly in parts pertinent to proteins that bind Activin A;

TGF-beta specific antibodies, peptibodies, related proteins, and the like, including but not limited to those described in U.S. Pat. No. 6,803,453 and U.S. Publication No. 2007/0110747, each of which is herein incorporated by reference in its entirety, particularly in parts pertinent to proteins that bind TGF-beta;

Amyloid-beta protein specific antibodies, peptibodies, related proteins, and the like, including but not limited to those described in PCT Publication No. WO 2006/081171, which is herein incorporated by reference in its entirety, particularly in parts pertinent to proteins that bind amyloid-beta proteins. One antibody contemplated is an antibody having a heavy chain variable region comprising SEQ ID NO:8 and a light chain variable region having SEQ ID NO:6 as disclosed in the foregoing publication;

c-Kit specific antibodies, peptibodies, related proteins, and the like, including but not limited to those described in U.S. Publication No. 2007/0253951, which is incorporated herein by reference in its entirety, particularly in parts pertinent to proteins that bind c-Kit and/or other stem cell factor receptors;

OX40L specific antibodies, peptibodies, related proteins, and the like, including but not limited to those described in U.S. Publication No. 2006/0002929, which is incorporated herein by reference in its entirety, particularly in parts pertinent to proteins that bind OX40L and/or other ligands of the OX40 receptor; and Other exemplary proteins, including Activase® (alteplase, tPA); Aranesp® (darbepoetin alfa); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4β7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-05 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Neulasta® (pegylated filgastrim, pegylated G-CSF, pegylated hu-Met-G-CSF); Neupogen® (filgrastim, G-CSF, hu-MetG-CSF); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP IIb/IIIa receptor monoclonal antibody); Actemra® (anti-IL6 Receptor mAb); Avastin® (bevacizumab), HuMax-CD4 (zanolimumab); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 146B7-CHO (anti-IL15 antibody, see U.S. Pat. No. 7,153,507);

Tysabri® (natalizumab, anti-α4integrin mAb); Valortim® (MDX-1303, anti-*B. anthracis* protective antigen mAb); ABthrax™; Vectibix® (panitumumab); Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Ra mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-α5β1 integrin mAb); MDX-010 (ipilimumab, anti-CTLA-4 mAb and VEGFR-1 (IMC-18F1); anti-BR3 mAb; anti-*C. difficile* Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxinl mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-1103); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); anti-LLY antibody; BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRα antibody (IMC-3G3); anti-TGFβ mAb (GC-1008); anti-TRAIL Receptor-2 human mAb (HGS-ETR2); anti-TWEAK mAb; anti-VEGFR/Flt-1 mAb; anti-ZP3 mAb (HuMax-ZP3); NVS Antibody #1; and NVS Antibody #2.

Also included can be a sclerostin antibody, such as but not limited to romosozumab, blosozumab, or BPS 804 (Novartis). Further included can be therapeutics such as rilotumumab, bixalomer, trebananib, ganitumab, conatumumab, motesanib diphosphate, brodalumab, vidupiprant, panitumumab, denosumab, NPLATE, PROLIA, VECTIBIX or XGEVA.

Additionally, included in the device can be a monoclonal antibody (IgG) that binds human Proprotein Convertase Subtilisin/Kexin Type 9 (PCSK9). Such PCSK9 specific antibodies include, but are not limited to, Repatha® (evolocumab) and Praluent® (alirocumab), as well as molecules, variants, analogs or derivatives thereof as disclosed in the following patents or patent applications, each of which is herein incorporated by reference in its entirety for all purposes: U.S. Pat. No. 8,030,547, U.S. Publication No. 2013/0064825, WO2008/057457, WO2008/057458, WO2008/057459, WO2008/063382, WO2008/133647, WO2009/100297, WO2009/100318, WO2011/037791, WO2011/053759, WO2011/053783, WO2008/125623, WO2011/072263, WO2009/055783, WO2012/0544438, WO2010/029513, WO2011/111007, WO2010/077854, WO2012/088313, WO2012/101251, WO2012/101252, WO2012/101253, WO2012/109530, and WO2001/031007.

Also included can be talimogene laherparepvec or another oncolytic HSV for the treatment of melanoma or other cancers. Examples of oncolytic HSV include, but are not limited to talimogene laherparepvec (U.S. Pat. Nos. 7,223,593 and 7,537,924); OncoVEXGALV/CD (U.S. Pat. No. 7,981,669); OrienX010 (Lei et al. (2013), World J. Gastroenterol., 19:5138-5143); G207, 1716; NV1020; NV12023; NV1034 and NV1042 (Vargehes et al. (2002), Cancer Gene Ther., 9(12):967-978).

Also included are TIMPs. TIMPs are endogenous tissue inhibitors of metalloproteinases (TIMPs) and are important in many natural processes. TIMP-3 is expressed by various cells or and is present in the extracellular matrix; it inhibits all the major cartilage-degrading metalloproteases, and may play a role in role in many degradative diseases of connective tissue, including rheumatoid arthritis and osteoarthritis, as well as in cancer and cardiovascular conditions. The amino acid sequence of TIMP-3, and the nucleic acid sequence of a DNA that encodes TIMP-3, are disclosed in U.S. Pat. No. 6,562,596, issued May 13, 2003, the disclosure of which is incorporated by reference herein. Description of TIMP mutations can be found in U.S. Publication No. 2014/0274874 and PCT Publication No. WO 2014/152012.

Also included are antagonistic antibodies for human calcitonin gene-related peptide (CGRP) receptor and bispecific antibody molecule that target the CGRP receptor and other headache targets. Further information concerning these molecules can be found in PCT Application No. WO 2010/075238.

Additionally, bispecific T cell engager (BiTE®) antibodies, e.g. BLINCYTO® (blinatumomab), can be used in the device. Alternatively, included can be an APJ large molecule agonist e.g., apelin or analogues thereof in the device. Information relating to such molecules can be found in PCT Publication No. WO 2014/099984.

In certain embodiments, the medicament comprises a therapeutically effective amount of an anti-thymic stromal lymphopoietin (TSLP) or TSLP receptor antibody. Examples of anti-TSLP antibodies that may be used in such embodiments include, but are not limited to, those described in U.S. Pat. Nos. 7,982,016, and 8,232,372, and U.S. Publication No. 2009/0186022. Examples of anti-TSLP receptor antibodies include, but are not limited to, those described in U.S. Pat. No. 8,101,182. In particularly preferred embodiments, the medicament comprises a therapeutically effective amount of the anti-TSLP antibody designated as A5 within U.S. Pat. No. 7,982,016.

Although the drug injection device, activation prevention features and/or mechanisms, methods, and elements thereof, have been described in terms of exemplary embodiments, they are not limited thereto. The detailed description is to be construed as exemplary only and does not describe every possible embodiment of the invention because describing every possible embodiment would be impractical, if not impossible. Numerous alternative embodiments could be implemented, using either current technology or technology developed after the filing date of this patent that would still fall within the scope of the claims defining the invention.

It should be understood that the legal scope of the invention is defined by the words of the claims set forth at the end of this patent. The appended claims should be construed broadly to include other variants and embodiments of same, which may be made by those skilled in the art without departing from the scope and range of equivalents of the device, activation prevention features and/or mechanisms, systems, methods, and their elements.

The patent claims at the end of this patent application are not intended to be construed under 35 U.S.C. § 112(f) unless traditional means-plus-function language is expressly recited, such as "means for" or "step for" language being explicitly recited in the claim(s). The systems and methods described herein are directed to an improvement to computer functionality, and improve the functioning of conventional computers.

What is claimed is:

1. A wearable drug delivery device, comprising:
   a housing;
   a reservoir adapted to store a drug product;
   a needle or cannula in fluid communication with the reservoir;
   an activator mechanism disposed on an external surface of the housing, the activator mechanism including an activator button and a stem at least partially extending out of the housing and connected to the activator button; and
   an activation prevention mechanism removably coupled to the housing and/or the activator mechanism to prevent inadvertent actuation of the activator mechanism, wherein the activation prevention mechanism is adapted to be at least partially disposed between the external surface of the housing and the activator mechanism; and
   wherein the activation prevention mechanism includes one of: (1) a plurality of forks defining a gap to accommodate an activator stem of the activator mechanism, at least one of the plurality of forks including a catch protruding inwardly; or (2) prongs to define a chamber to receive the activator mechanism.

2. The wearable drug delivery device of claim 1, wherein the activation prevention mechanism comprises a gripping portion for selectively removing the activation prevention mechanism from the injector housing and/or the activator mechanism.

3. The wearable drug delivery device of claim 2, wherein the gripping portion of the activation prevention mechanism includes an integral tab comprising either (a) a rigid tab, or (b) a flexible tab.

4. The wearable drug delivery device of claim 1, wherein the activator button is a manually depressible activator button, and wherein the activation prevention mechanism comprises:
   a coupling portion removably coupled to the activator button between the activator button and the housing to prevent the activator button from being depressed.

5. The wearable drug delivery device of claim 4, wherein a plurality of forks reside between the button and the housing to prevent actuation.

6. The wearable drug delivery device of claim 1, wherein the activation prevention mechanism includes a securing portion engaging the housing for proper positioning of the activation prevention mechanism and/or for securing the activation prevention mechanism to the housing.

7. The wearable drug delivery device of claim 6, wherein the securing portion includes a tab with a surface contoured to a corresponding surface of the housing.

8. The wearable drug delivery device of claim 1, wherein the activator button is a manually depressible activator button, and
   wherein the activation prevention mechanism comprises a frame portion at least partially enclosing the activator button to prevent inadvertent manipulation of the activator mechanism.

9. The wearable drug delivery device of claim 8, wherein the frame portion comprises a front wall portion and lateral side prongs that define a chamber therebetween sized to receive the activator button therein.

10. The wearable drug delivery device of claim 9, wherein at least one of the front wall portion or the lateral side prongs include catches that extend along opposite sides of the activator button to hold the frame portion on the activator button.

* * * * *

UNITED STATES PATENT AND TRADEMARK OFFICE
CERTIFICATE OF CORRECTION

| | | |
|---|---|---|
| PATENT NO. | : 11,590,277 B2 | Page 1 of 1 |
| APPLICATION NO. | : 16/488120 | |
| DATED | : February 28, 2023 | |
| INVENTOR(S) | : Stonecipher et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 77 days.

Signed and Sealed this
Seventh Day of January, 2025

Derrick Brent
*Acting Director of the United States Patent and Trademark Office*